(12) United States Patent
Mikol et al.

(10) Patent No.: US 10,709,475 B2
(45) Date of Patent: Jul. 14, 2020

(54) PUMPING SURGICAL CANNULA

(71) Applicants: Edward J. Mikol, Myrtle Beach, SC (US); Hung T. Than, Rockville, MD (US)

(72) Inventors: Edward J. Mikol, Myrtle Beach, SC (US); Hung T. Than, Rockville, MD (US)

(73) Assignee: Edward J. Mikol, Myrtle Beach, SC (US)

( * ) Notice: Subject to any disclaimer, the term of this patent is extended or adjusted under 35 U.S.C. 154(b) by 136 days.

(21) Appl. No.: 15/914,028

(22) Filed: Mar. 7, 2018

(65) Prior Publication Data
US 2019/0274724 A1    Sep. 12, 2019

(51) Int. Cl.
| A61B 17/34 | (2006.01) |
| A61B 17/02 | (2006.01) |
| A61M 13/00 | (2006.01) |
| A61B 17/00 | (2006.01) |

(52) U.S. Cl.
CPC ...... *A61B 17/3439* (2013.01); *A61B 17/0218* (2013.01); *A61B 17/3421* (2013.01); *A61B 17/3423* (2013.01); *A61M 13/003* (2013.01); *A61B 17/3498* (2013.01); *A61B 2017/00557* (2013.01); *A61B 2017/0225* (2013.01); *A61B 2017/3419* (2013.01)

(58) Field of Classification Search
CPC ............ A61B 17/3423; A61B 17/0218; A61B 17/3498; A61B 17/3421; A61B 17/3439; A61B 2017/00557; A61B 2017/3419; A61B 2017/0225; A61B 2017/349; A61B 2017/3486; A61M 13/003
See application file for complete search history.

(56) References Cited

U.S. PATENT DOCUMENTS

| 4,177,815 A   | 12/1979 | Patel |
| 5,163,949 A   | 11/1992 | Bonutti |
| 5,226,876 A * | 7/1993  | Filipi ............... A61B 17/3421 604/174 |
| 5,320,611 A   | 6/1994  | Bonutti |
| 5,624,399 A   | 4/1997  | Ackerman |
| 5,632,761 A   | 5/1997  | Smith et al. |
| 5,634,937 A   | 6/1997  | Mollenauer et al. |
| 5,683,364 A * | 11/1997 | Zadini ............... A61B 17/0218 604/272 |
| 5,685,826 A   | 11/1997 | Bonutti |
| 5,839,715 A   | 11/1998 | Leinsing |

(Continued)

OTHER PUBLICATIONS

International Search Report and Written Opinion issued in connection with the corresponding International Application No. PCT/US2019/19939 dated May 15, 2019.

*Primary Examiner* — Kevin T Truong
*Assistant Examiner* — Tracy L Kamikawa
(74) *Attorney, Agent, or Firm* — The H.T. Than Law Group

(57) ABSTRACT

Disclosed herein are multiple cannulas defining a lumen sized and dimensioned to receive one or more medical instruments, an inflatable outer membrane attached to an outer surface of the cannula, and at least one activator that reversibly activates the cannulas to push a fluid contained in the cannulas into the outer membrane to fill or pressurize the outer membrane. Also disclosed are methods for operating these cannulas.

17 Claims, 28 Drawing Sheets

(56) References Cited

U.S. PATENT DOCUMENTS

| | | | |
|---|---|---|---|
| 6,129,706 | A | 10/2000 | Janacek |
| 6,283,971 | B1 * | 9/2001 | Temeles ............. A61B 17/1666 606/79 |
| 6,440,120 | B1 | 8/2002 | Maahs |
| 6,443,159 | B1 | 9/2002 | Fogarty et al. |
| 6,468,292 | B1 | 10/2002 | Mollenauer et al. |
| 6,723,053 | B2 | 4/2004 | Ackerman et al. |
| 7,198,632 | B2 | 4/2007 | Lim et al. |
| 7,563,250 | B2 | 7/2009 | Wenchell |
| 7,998,113 | B2 | 8/2011 | Swisher |
| 8,066,673 | B2 | 11/2011 | Hart et al. |
| 8,382,707 | B2 | 2/2013 | Albrecht et al. |
| RE44,380 | E | 7/2013 | De la Torre et al. |
| 8,491,533 | B2 | 7/2013 | Parihar et al. |
| 8,679,053 | B2 | 3/2014 | von Segesser |
| 8,795,326 | B2 | 8/2014 | Richard |
| 9,161,747 | B2 | 10/2015 | Whittaker et al. |
| 2004/0138702 | A1 | 7/2004 | Peartree et al. |
| 2009/0275898 | A1 | 11/2009 | Wenchell |
| 2016/0331401 | A1 | 11/2016 | Dreyfuss et al. |
| 2017/0135687 | A1 * | 5/2017 | Pacak ................... A61B 17/34 |
| 2017/0135721 | A1 | 5/2017 | Pacak et al. |
| 2019/0059937 | A1 * | 2/2019 | Buyda ................ A61B 17/3423 |

* cited by examiner

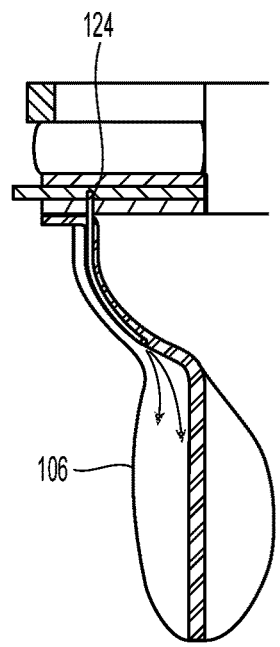
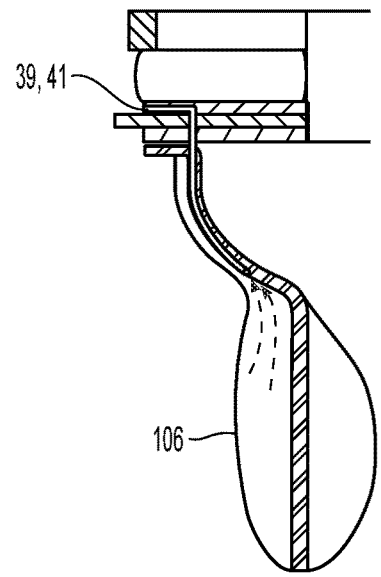
Fig. 9A                    Fig. 9B
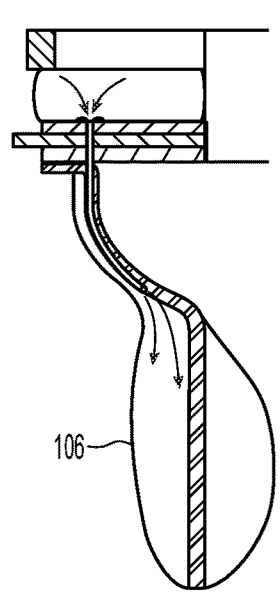
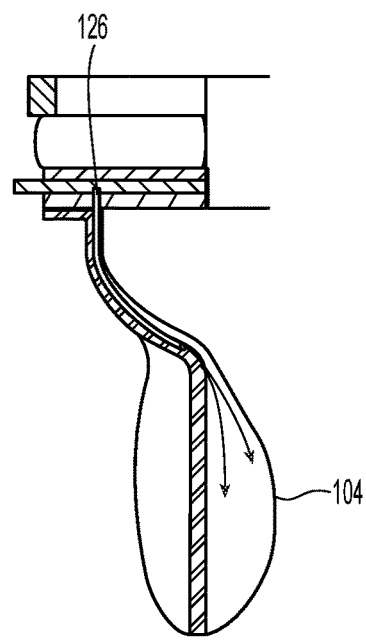
Fig. 9C                    Fig. 9D

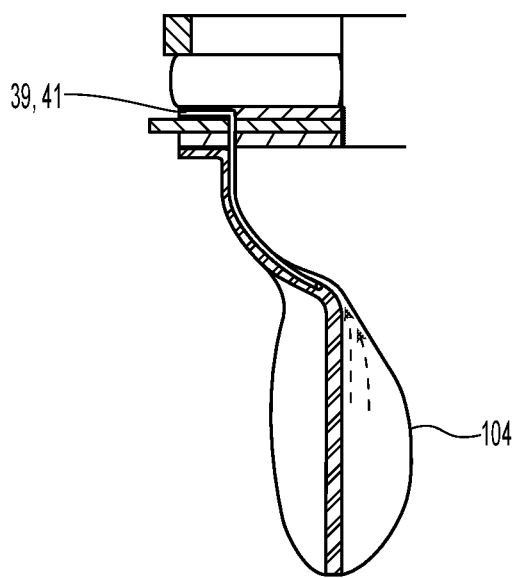
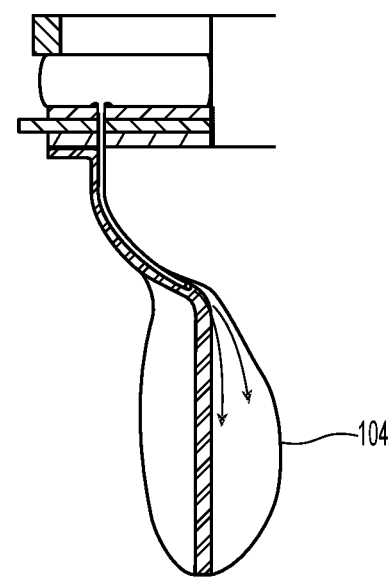
*Fig. 9E*        *Fig. 9F*
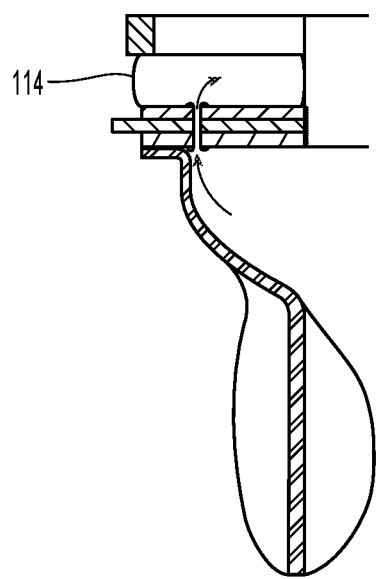
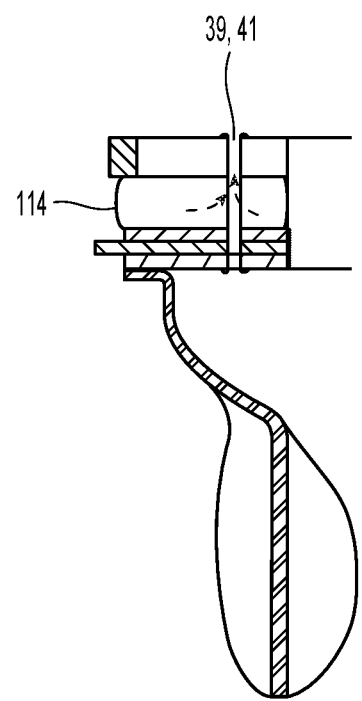
*Fig. 9G*        *Fig. 9H*

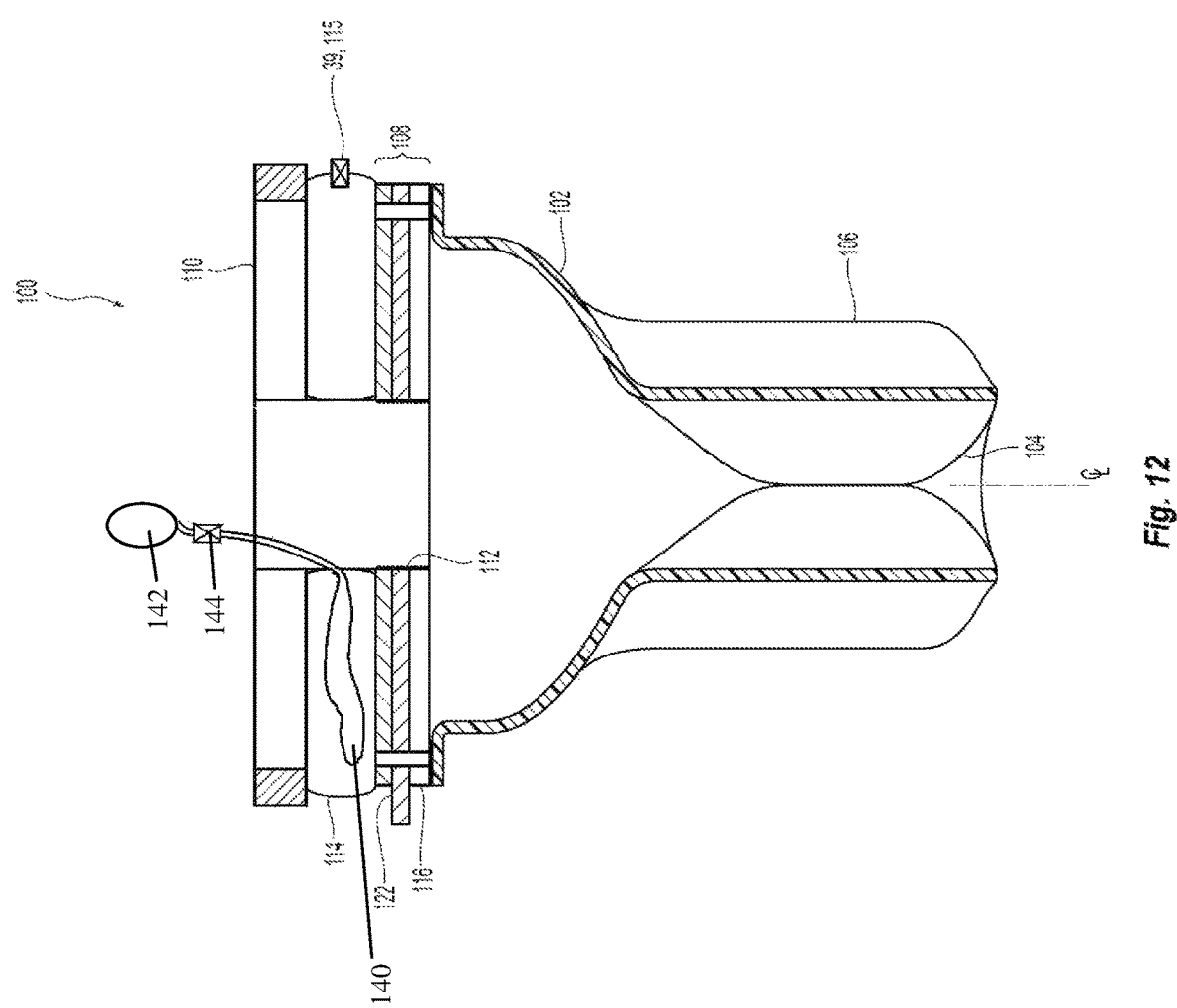

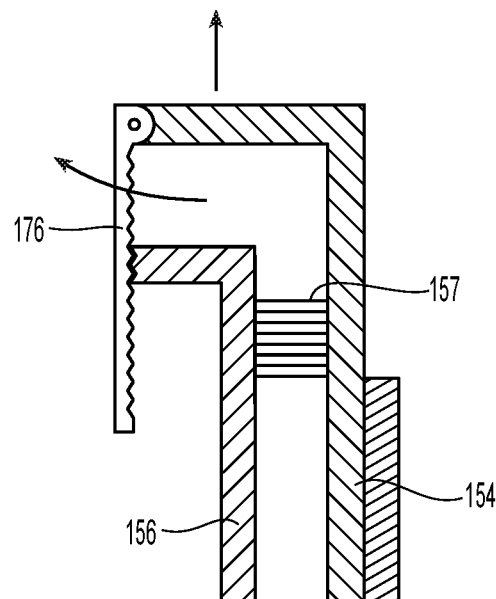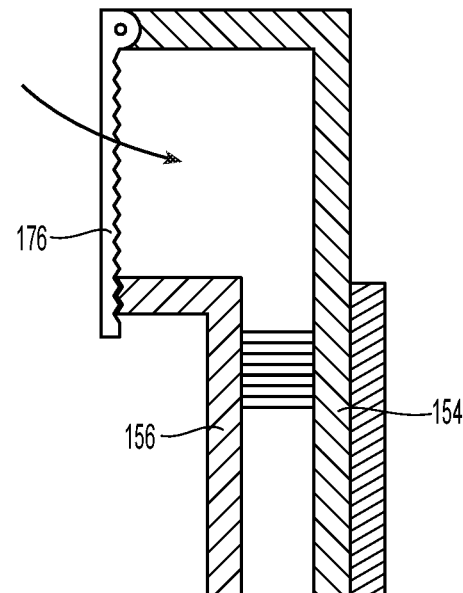
*Fig. 15A*      *Fig. 15B*
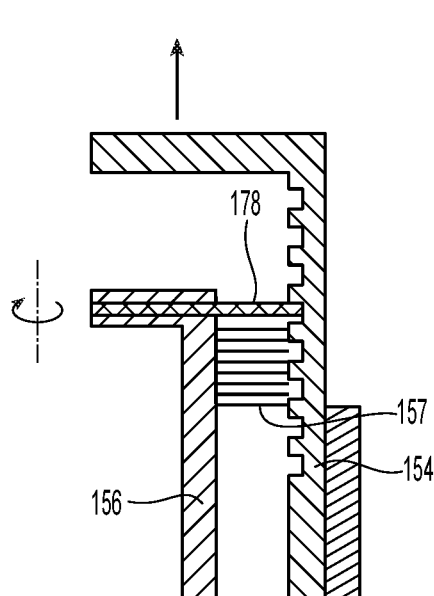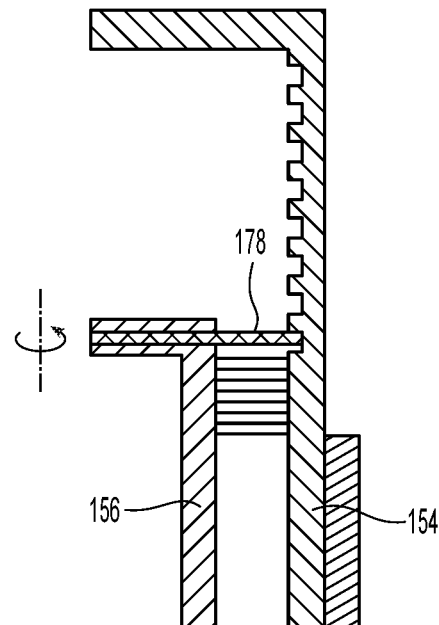
*Fig. 16A*      *Fig. 16B*

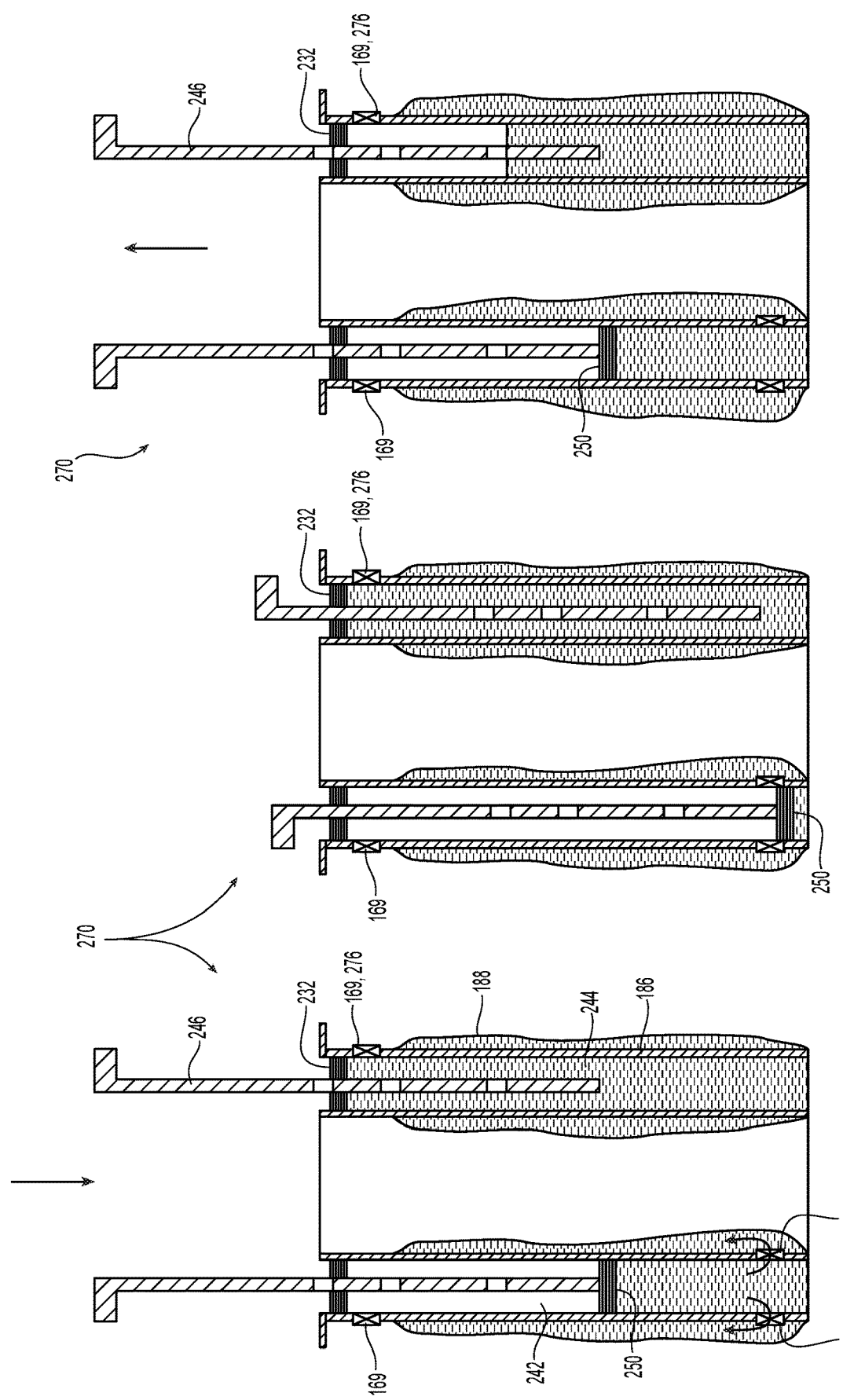

PUMPING SURGICAL CANNULA

FIELD OF THE INVENTION

The present invention is directed to a surgical cannula with an improved ability to anchor and/or seal to the incision site and to the surgical instrument(s) inserted therethrough. The inventive surgical cannula can individually control various flow/vent paths to allow discrete controls of the outer anchor/seal membrane and the inner sealing membrane.

BACKGROUND OF THE INVENTION

Cannulas have been used in minimally invasive surgical procedures, such as laparoscopic and arthroscopic surgeries. Typically, in these procedures a small incision in made in the skin of a patient to access internal cavities, such as the abdomen or joints. A cannula is inserted into and is secured to the incision site. Surgical instruments are passed through the proximal openings of cannulas to enter a body cavity. During these procedures, the body cavity is inflated with an insufflated gas or liquid to create a surgical zone in the body cavity for surgical instruments. These cannulas generally have sealing members to seal the cannula to the incision site U.S. patent application publication No. 2009/0275898 to Wenchell discloses a cannula with an internal inflatable membrane in its lumen. Insufflated gas enters the proximal end of the cannula to inflate the internal membrane to seal the lumen with or without a medical instrument therein. However, the pressure within the inflated membrane with the insufflated gas would be the same as the pressure within the body cavity with the insufflated gas, i.e., both would have the same pressure of the insufflated gas. This is less than ideal because there is no positive pressure gradient from the inflated internal membrane to the body cavity for a positive seal.

U.S. Pat. No. 9,161,747 to Whittaker et al discloses a cannula with a plurality of protrusions located on the cannula's outer surface. These protrusions are extended outward against the incision site when a collar or a cam is rotated or a telescoping sleeve is pulled relative to the cannula. These anchoring protrusions are rigid and are pressed against the incision site, which may cause post-procedure discomfort for the patient.

Hence, there remains a need for an improved surgical cannula that resolves these issues.

SUMMARY OF THE INVENTION

The invention is directed to an improved surgical cannula that overcomes the prior art drawbacks identified above.

The inventive cannula has an inflatable membrane or channel(s) on its outer surface that when inflated can anchor/seal the cannula to the tissues surrounding the incision site, and/or another inflatable membrane in its internal lumen that when inflated can seal the lumen and/or seal medical instruments inserted into and through the cannula to treat patients.

The inventive cannula preferably and advantageously uses any fluid or liquid including but not limited to an external fluid or an insufflated fluid, i.e., the fluid pumped into a body cavity, to fill the membranes or channels on the cannula. The filled fluid is then pressurized to inflate or to increase its volume to anchor/seal the cannula to the incision site, and/or to seal the internal lumen.

An embodiment of the present invention is directed to a cannula adapted to be inserted into a body cavity comprising a lumen wall and an outer casing positioned spaced apart from each other defining a fluid chamber therebetween, a flow piston connected to a sealing member which is positioned inside the fluid chamber, and an outer membrane connected to outer casing. The fluid chamber is fluidly connected to the outer membrane through a casing one-way valve. In a priming configuration the fluid chamber is filled with a fluid, and in a pressurizing configuration the flow piston is moved in a second direction to move the fluid from the fluid chamber into the outer membrane through the casing one-way valve.

In one embodiment, the fluid chamber is fluidly connected to the body cavity by a reservoir one-way valve, and wherein in the priming configuration the flow piston is moved in a first direction to move fluid into the fluid chamber through the reservoir one-way valve. In another embodiment, the fluid chamber is pre-filled before insertion into the body cavity with an external fluid.

The cannula may also comprise a lumen membrane connected to the lumen wall and the fluid chamber is fluidly connected to the lumen membrane through a lumen valve, and in the pressurizing configuration the fluid is pushed into the lumen membrane through the lumen one-way valve.

In one embodiment, the lumen valve may comprise a one-way valve. In another embodiment, the flow piston is located adjacent to the lumen wall and the flow piston comprises at least one piston port and the lumen wall comprises at least one lumen port. In the priming configuration, the at least one piston port and the at least one lumen port align with each other to form an open state of the lumen valve and in the pumping state the at least one piston port and the at least one lumen port misalign with each other to form a close state of the lumen valve.

The cannula may also comprise a drainage channel, which is fluidly connected to outer membrane by a valve and wherein said valve can be opened by an activator to drain the fluid from the outer membrane to the drainage channel. Alternatively, the drainage channel is fluidly connected to outer membrane by a drainage opening, wherein the opening is sealed by a drainage sealing member in the pressurizing configuration and in a drainage configuration the drainage sealing member is moved to expose the drainage opening.

The first direction is a distal direction and the second direction is a proximal direction, or vice versa. Either the at least one of the casing one-way valve or the reservoir one-way valve is a flapper valve, or both can be flapper valves. The reservoir one-way valve may be located proximate a distal end of the cannula. Alternatively, the cannula may have a second sealing member to provide a seal for the fluid chamber and the reservoir one-way valve is located proximate a proximal end of the cannula.

In any cannula described and claimed herein, the outer membrane may be made from an elastomeric material, and the cannula may comprise a vent valve positioned to vent the outer membrane. The vent valve further may also comprise a first vent in fluid communication with the outer membrane and a second vent in fluid communication with the first vent. A user-actuatable normally closed valve may be positioned in the second vent. A membrane may fluidically connect the first vent to the second vent and isolate the first and second vents from other chamber and conduit in the cannula.

Another embodiment of present invention is directed to a cannula comprising a lumen wall defining at least one lumen port, a flow piston positioned on the outside of the lumen wall and defining at least one piston port, an outer casing positioned spaced apart from the flow piston to define a fluid chamber therebetween and an outer membrane connected to outer casing. The outer casing defines at least one casing port to fluidly connect the outer membrane to the fluid chamber. In a filling configuration the at least one lumen port aligns with the at least one piston port to allow a fluid to enter the fluid chamber and the outer membrane, and in a pressurizing configuration the at least one lumen port misaligns with the at least one piston port and the flow piston is moved to move fluid from the fluid chamber to the outer membrane to secure the cannula to an incision site.

The flow piston may be attached to a distal sealing member and the outer casing is attached to a proximal sealing member, such that the fluid chamber is further defined between the proximal sealing members and the distal sealing member, and the distal sealing member is moved toward the proximal sealing member in the pressurizing configuration.

The outer casing may comprise a first vent to vent gas within the outer membrane in the filling configuration. The outer casing may comprise a second vent to vent gas from the fluid chamber in the filling configuration. Preferably, a one-way valve is disposed in the second vent. The flow piston may further comprise a vent sealing member configured to seal the second vent in the pressurizing configuration. The outer membrane may depressurize when the cannula moves from the pressurizing configuration to the filling configuration. The cannula may also comprise a latch to maintain the cannula in the pressuring configuration.

Another embodiment of the present invention is directed a method for operating a cannula comprising the steps of
 a. inserting the cannula into a body cavity,
 b. filling an internal fluid chamber of the cannula with an insufflated fluid from the body cavity,
 c. filling said insufflated fluid from the internal fluid chamber to an outer membrane of the cannula, and
 d. optionally increasing a pressure inside the outer membrane above a pressure of the insufflated fluid.

In one version, step (b) of the method comprises a step of venting the cannula and allowing the insufflated fluid to enter the internal fluid chamber. Optionally, after step (b) and before step (c) the method may also have step (b.2) to isolate the internal fluid chamber from the body cavity, and/or step (b.3) to stop the venting. In this version when step (d) is required, it comprises a step of moving a piston in either a proximal or a distal direction.

In another version, step (b) of this method comprises a pumping of the insufflated fluid into the internal chamber. The pumping step may comprise a step of moving a piston in either a proximal or a distal direction. Step (c) may comprise a step of moving the piston in an opposite direction. In this version when step (d) is required, it comprises a step of moving a piston in the opposite direction.

In yet another embodiment, the cannula comprises a plurality of concentric tubular members. The inner compression sleeve is sized and dimensioned to compress the inner lumen membrane to increase its pressure and its width, and the outer compression sleeve is sized and dimensioned to compress and expand the anchor/seal the outer membrane or channel to increase its pressure and its width to secure/anchor/seal the cannula to the tissues surrounding the incision. The fluid, which can either be liquid or gas, preferably liquid, used to inflate the cavity, preferably enters the cannula to fill the inner lumen membrane and the outer membrane/channel after the cannula is inserted through the incision into the body cavity. Between the compression inner and outer sleeves is a lumen wall located adjacent to the inner compression sleeve and is in fluid communication with the lumen membrane, a flow sleeve with flow channels defined thereon, and an anchor/seal sleeve in fluid communication with the anchor channel. The lumen wall, the flow sleeve and the anchor/seal sleeve are rotated relative to each other to select flow channels.

In another embodiment, the flow sleeve is omitted to minimize the thickness of the cannula and the flow channels can be etched on either the lumen and/or the anchor sleeve. The etched channels are not cut through the thickness of the lumen or anchor sleeve, but are only partially cut through the wall of the lumen and/or anchor sleeve to form flow channels.

In another embodiment, the invention is also directed to a similar cannula where the inner and outer compression sleeves are omitted and is replaced by a bellows or syringe that is filled with a pressurizing fluid, preferably the insufflated fluid. The bellows is compressed or squeezed to inject the pressurizing fluid into the inner membrane and/or outer membrane or channel.

In another embodiment, the inventive cannula comprises a lumen with multiple flow channels defined within the wall of the lumen or defined thereon. The lumen is attached at the proximal end to a manifold, a bellows and a rotating cap. The manifold comprises layers that are rotatable relative to each other. One layer defines various ports that are connected to the flow channels defined in or on the lumen wall. Another layer is rotatable to select which port(s) to open or close to effect flow into the inner lumen membrane, the outer anchor/seal membrane and the bellows. The cap is rotated toward the manifold to squeeze the fluid from the bellows into one or both membranes to pressurize same.

In another embodiment, the cannulas of the present invention can be manufactured by 3-D printing in whole or in part, preferably, the portion(s) of the cannulas that contain flow channels. An advantage of 3-D printing is that the sidewall of the lumen of the cannula can be printed to be thin with flow channels to minimize the incision size.

Another embodiment that has a means to fill the bellows externally (rather than with cavity fluid), which is used to fill the anchor and/or lumen membranes and is then pressurized.

These and other objects of the present invention are realized by a cannula comprising a casing defining a lumen sized and dimensioned to receive one or more medical instruments, a flexible bellows, an inflatable outer membrane attached to an outer surface of the casing, at least one flow channel fluidly connecting the bellows to the outer membrane, and at least one activator that reversibly activates the bellows to push a fluid contained in the cannula into the outer membrane to fill or pressurize the outer membrane.

In one embodiment, the bellows can be filled with the fluid through an external valve fluidly connected to the bellows, and/or can be filled with insufflated fluid from the body cavity. The at least one activator activates the bellows by compressing it to push the fluid contained therein into the outer membrane to pressurize the outer membrane, and deactivates the bellows by allowing the bellows to expand to pull the fluid contained in the outer membrane to depressurize the outer membrane.

In another embodiment, an inner bellows is provided within the bellows and the at least one activator activates by expanding the inner bellows to push the fluid contained in the space between the inner bellows and the bellows, which acts as an outer container for the fluid, into the outer membrane. The at least one activator deactivates by allowing the inner bellows to collapse to pull fluid contained in the outer membrane into the bellows/outer container.

The cannula may further comprise a flow selector, wherein the flow selector is actuatable to open or close the at least one flow channel. The at least one flow channel is located on or within the casing. The cannula is insertable into body cavity through an incision site and is wedged within the incision site and the fluid comprises an insufflated fluid from the body cavity.

The fluid in the outer membrane is preferably pressurized above a pressure of an insufflated fluid. The cannula may further comprise an inner membrane inflatable with the fluid to seal the lumen with or without the one or more medical instruments disposed therein.

The flow selector may comprise a dial disposed proximate to a proximal end of the cannula. The at least one flow channel may comprise a plurality of flow channels, and the dial may comprise a rotatable layer overlying a port layer comprising a plurality of ports corresponding with and selectively in fluidic communication with said plurality of flow channels, wherein the rotatable layer is rotated to select the ports and the flow channels to open or close.

The dial may comprise a plurality of tabs. A first tab is rotatable to fill or seal the outer membrane. A second tab is rotatable to fill or seal an inner membrane disposed in the lumen. A
third tab is rotatable to fill or seal the bellows.

The port layer comprises a bellows port allowing an insufflated fluid to enter the bellows. The port layer may be organized into a plurality of groups of ports and the rotatable layer is rotated a distance equal to a distance of a group of ports to selectively open and close one group of ports. Alternatively, the port layer is rotated an angular distance sufficient to move from one port to another port to selectively open and close said one port or said another port.

The at least one activator can be a rotatable cap. The casing can be 3-D printed. The casing may comprise at least a first casing and a second casing layer and the at least one flow channel is etched into the first casing layer and is covered by the second casing layer. The first casing layer is rotatable relative to the second casing layer so selectively open or close the at least one flow channel.

Another embodiment of the inventive cannula comprising a casing defining a lumen sized and dimensioned to receive one or more medical instruments, an inflatable outer membrane attached to an outer surface of the casing, a plurality of flow channels formed on or within the casing, wherein at least one flow channel is fluidly connected to the outer membrane to inflate the outer membrane and at least one flow channel is fluidly connected to the outer membrane to pressurize and/or to vent the outer membrane, a flow selector to select one or more flow channels, and a pressure source selectively connected to the outer membrane to pressurize the outer membrane, wherein the outer membrane is filled with a fluid after the cannula is inserted into an incision site, and the pressure source pressurizes the outer membrane above a pressure of an insufflated fluid to maintain the cannula within the incision site.

The casing comprises at least a first casing and a second casing layer, and the at least one flow channel is etched into the first casing layer and is covered by the second casing layer. The first casing layer is rotatable relative to the second casing layer so selectively open or close the plurality of flow channels.

The flow selector comprises a first control dial and a second control dial and wherein the first casing layer and the second casing layer are connected to the first control dial and the second control dial, respectively. A port allowing the insufflated fluid to enter the outer membrane is located at a distal end of the casing. The pressure source comprises a rigid sleeve displacing the insufflated fluid into the outer membrane.

Another embodiment of the present invention is directed to a method for operating a cannula comprising the steps of
 a. inserting the cannula into an incision site,
 b. filling an outer membrane of the cannula with a fluid,
 c. sealing said outer membrane, and
 d. increasing a pressure inside the outer membrane above a pressure of an insufflated fluid.

The step (d) may comprise a step of pumping another amount of fluid into the outer membrane. The step of pumping may comprise a step of activating a bellows to push another amount of fluid into the outer membrane. In one alternative, a rotating mechanism compresses the bellows. The inventive method may further comprise a step (e) of rotating a rotatable layer to select between step (b), (c) or (d).

BRIEF DESCRIPTION OF THE DRAWINGS

In the accompanying drawings, which form a part of the specification and are to be read in conjunction therewith and in which like reference numerals are used to indicate like parts in the various views:

FIGS. 9A-9H are partial cross-sectional views of various ports A-H and their respective fluidic connections;

FIG. 12 is a cross-sectional view of another inventive cannula;

FIGS. 15A-B are partial cross-sectional views of the embodiment shown in FIGS. 13 and 14 showing a latching mechanism;

FIGS. 16A-B are partial cross-sectional views of another latching mechanism;

FIGS. 23B-E are lengthwise cross-sectional views of a sequence of operation of this hybrid cannula.

DETAILED DESCRIPTION OF THE PREFERRED EMBODIMENTS

Parts List

Figure 1:
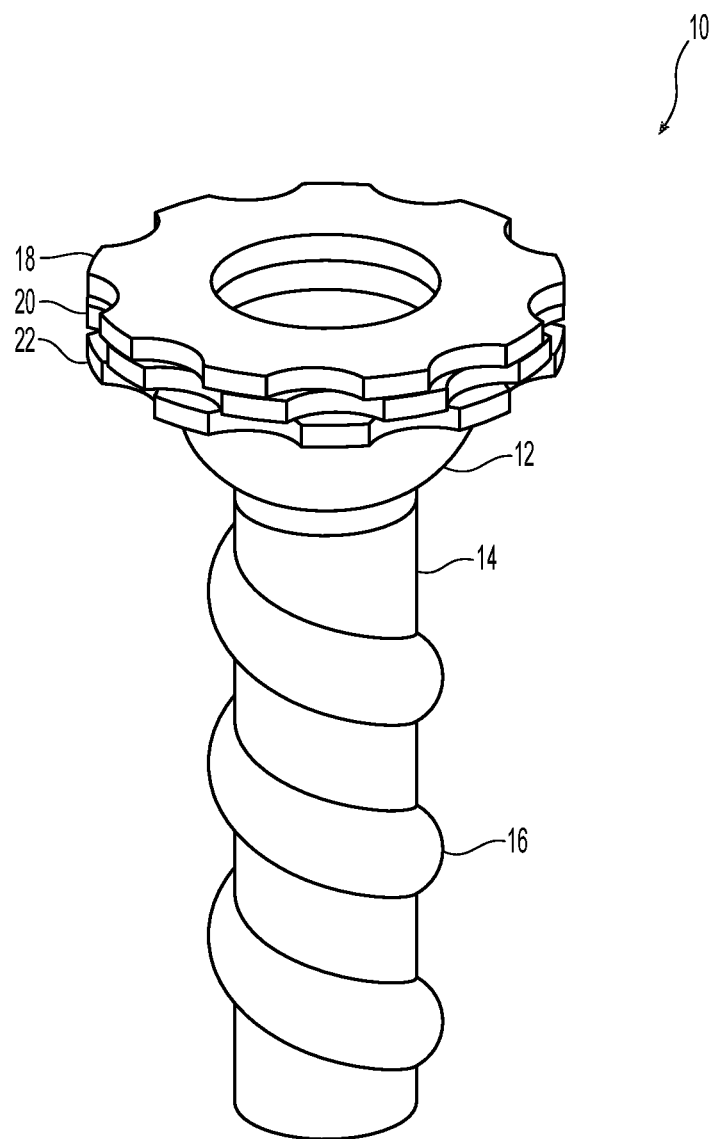
FIG. 1 is a perspective view of an exemplary embodiment of the inventive cannula.

10 Inventive cannula
12 Outer compression sleeve
14 Anchor sleeve
16 Anchor channel
18 Control dial
20 Control dial
22 Control dial
24 Flow sleeve
26 Lumen wall, lumen body or external casing
28 Ingress
30 Egress
32 Ingress
34 Egress
36 Lumen membrane
38a, b Inflating flow channel
39, 39a, 39b Duckbill valve
40 Deflating flow channel
41 Vent
42 Seal area
44 Insufflation fluid
46 Inner compression sleeve
48 Inflating flow channel
50 Connecting flow channel
52 Inflating flow channel
100 Cannula
102 Lumen wall, lumen body or external casing
104 Inner lumen membrane
106 Outer anchor/seal membrane
108 Manifold
110 Rotating cap
112 Threaded connector
114 Bellows
115 External valve or seal, such as sealing stopper
116 Covering or port layer
118 Ports A-I
120 Tabs O, I, B
122 Rotating layer
124-128 Flow channels
130 Segments
130 a,b,c End segments
132-136 Segment group or group of one or more ports
138 Flow channels
140 Internal bellows
142 Pump
144 Valve
150 Cannula
152 Lumen wall
154 Flow piston
155 Distal sealing member
156 Outer casing
157 Proximal sealing member
158 Outer anchor membrane
159 Return spring
160 Fluid chamber
162 Lumen ports
164 Piston ports
166 Outer casing ports
168 First vent
169 Normally closed valve
170 Second vent
172 Piston sealing member
174 Counter-balance member
176 Rotatable latch
178 Rotatable latch
180 Cannula
182 Lumen wall
184 Flow piston
186 Outer casing
185 Distal seal
187 Lumen membrane
188 Outer anchor membrane
190 Flow chamber/reservoir
192 Reservoir one-way valve
194 Lumen one-way valve
196 Casing one-way valve
200 Flapper valve
202 Flapper
204 Valve opening
206 Live joint
212 Drainage channel
214 Lumen one-way drainage valve or opening
216 Casing one-way drainage valve or opening
217 One-way drainage valve or opening
234 Flow holes in flow piston 184
218 Drainage valve activator
222, 224 Drainage piston activator
226 Biasing spring
230 A variation of cannula 180
232 Proximal seal 240 Pre-filled cannula
242, 244 First, second flow chamber
246 Piston
248 Rotatable pusher
250, 252 Sealing member
254, 256 One-way valve
258, 260 One-way valve
270 Pre-filled cannula, external pumping cannula
272 One-way valve Referring to FIG. 1, inventive cannula 10 is shown with outer compression sleeve 12 and anchor/seal sleeve 14. Anchor/seal sleeve 14 preferably has a spiral shaped anchor channel 16 wrapped therearound. It is noted that anchor channel 16 may have any shape and may comprise multiple individual channels, and the present invention is not limited thereto. Alternatively, anchor channel 16 is replaced by an anchor membrane similar to that shown in FIGS. 7-9. A number of control dials are also shown, and preferably three control dials 18, 20 and 22 are used and are described further below.

Figure 2C:
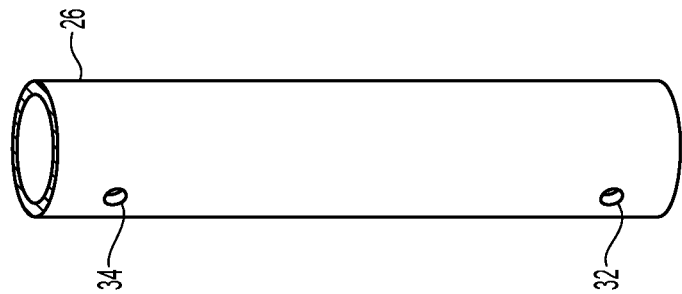
FIG. 2C is a perspective cut-away view of the lumen with selected components omitted for clarity.
Figure 2B:
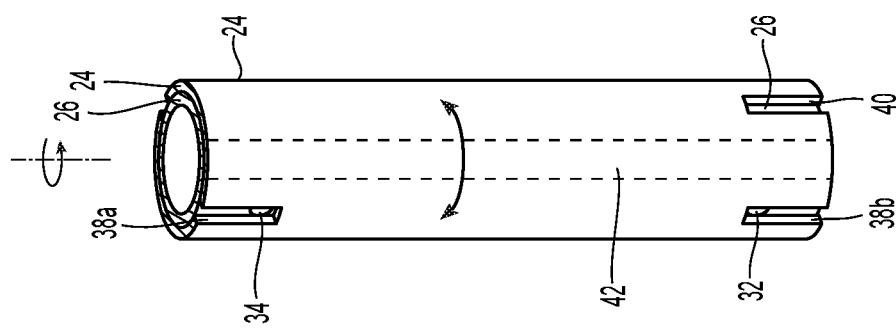
FIG. 2B is a perspective cut-way view of a portion of the cannula showing the flow sleeve with selected components omitted for clarity.
Figure 2A:
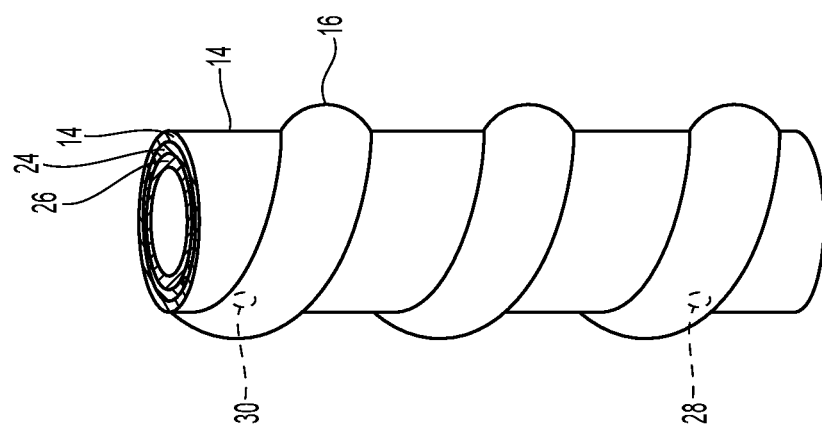
FIG. 2A is a perspective cut-way view of a portion of the cannula showing the anchor sleeve with selected components omitted for clarity.

Referring to FIGS. 2A-2C, anchor sleeve 14 is located concentrically outside of flow sleeve 24, which is located concentrically outside of lumen wall 26. Anchor sleeve 14 is in fluid communication with anchor/seal channel 16 via ingress 28 and egress 30. Lumen wall 26 also has ingress 32 and egress 34, which are in fluid communication with lumen membrane 36 shown in FIGS. 3A-3E. Flow sleeve 24 preferably comprises a number of flow channels, such as inflating flow channels 38a and 38b which are aligned with each other, preferably vertically aligned with each other, and deflating flow channel 40, as shown. Flow sleeve 24 is rotatable relative to anchor/seal sleeve 14 and lumen 26, so that the flow channels may align with the ingress and egress ports to inflate or deflate the anchor channel 16 and lumen membrane 36, as discussed below.

Figure 3C:
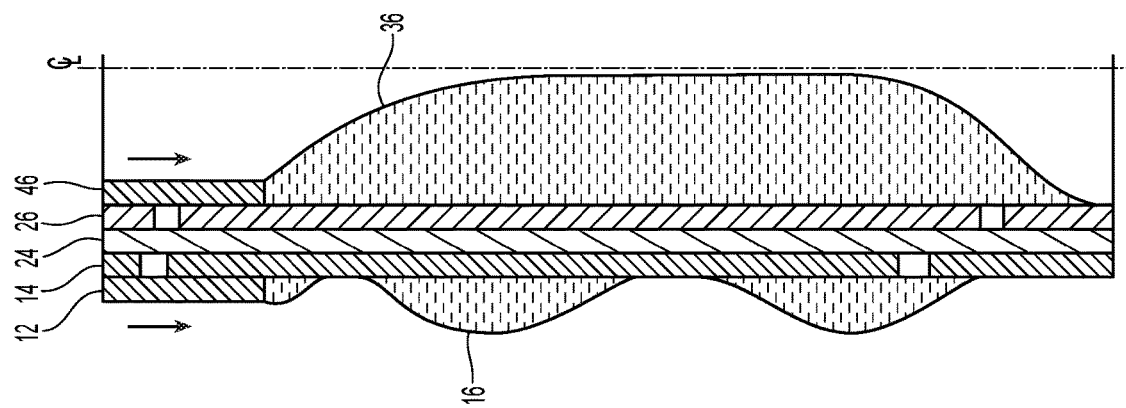
FIG. 3C is the cannula of FIG. 3A showing the compression sleeves compressing the lumen membrane and the anchor channel.
Figure 3B:
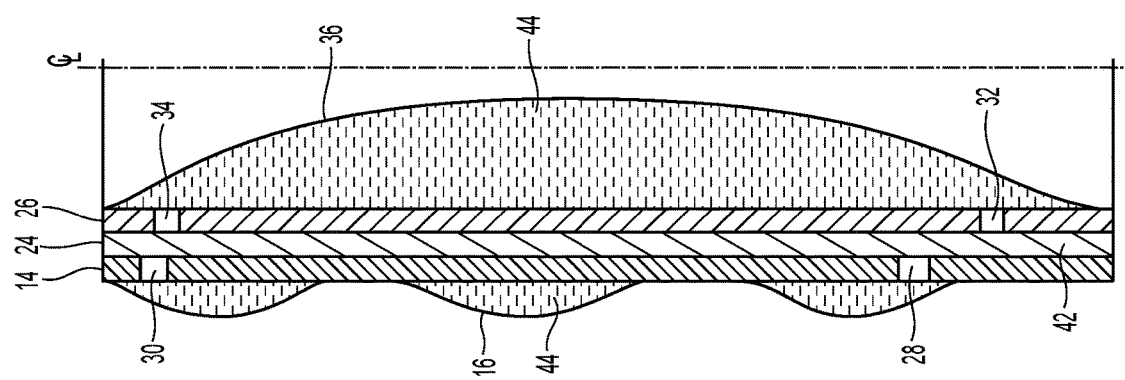
FIG. 3B is the cannula of FIG. 3A showing the cannula being sealed.
Figure 3A:
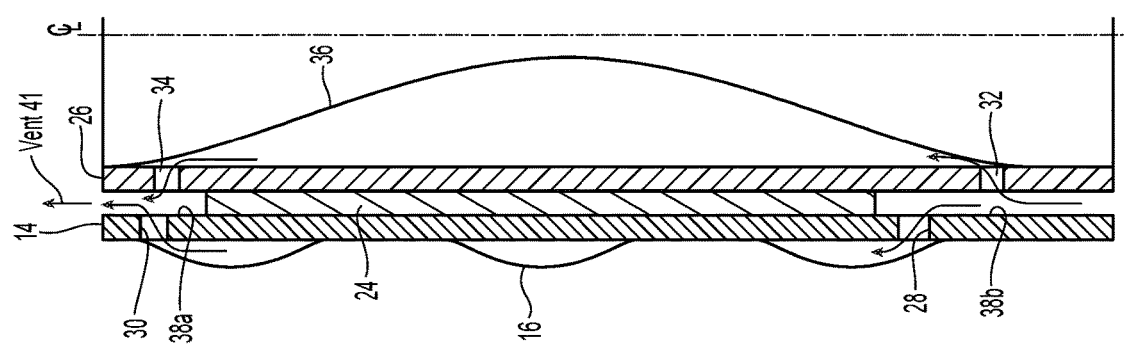
FIG. 3A is a partial cross-sectional view of the anchor sleeve, flow sleeve and lumen showing the cannula being inflated.

Referring to FIG. 3A (partial cross-sectional view), to inflate cannula 10 flow sleeve 24 is rotated to align flow channel 38b to align with ingress 28 and 32 and flow channel 38a with egress 30 and 34 of anchor sleeve 14 and lumen 26, respectively. Cavity or insufflated fluid pumped into the cavity by an orthopedic or another medical pump enters cannula 10 through flow channel 38b and through ingress ports 28 and 32 to anchor channel 16 and lumen membrane 36, respectively, to inflate same. The cavity fluid exits anchor channel 16 and lumen membrane 36 through egress ports 30 and 34, respectively, into flow channel 38a. Preferably, flow channel 38a is connected to a vent 41 disposed on the top or proximal end of cannula 10, or a vacuum source, such as a syringe or a pump attached to cannula 10. Preferably, this vent terminates with a flapper valve or the like, which allows air within the flow channels, anchor channel 16 and/or lumen membrane 36 to escape but closes when the cavity liquid reaches the flapper valve.

Figure 6A:
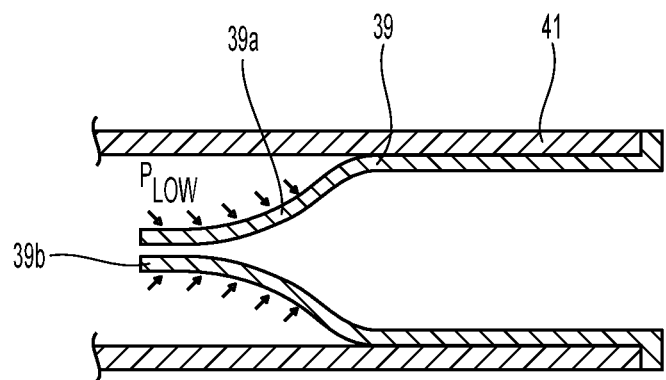
FIGS. 6A and 6B are cross-sectional view of an exemplary one-way valve, such as a duckbill valve inside a vent.

In one embodiment, the vent 41 terminates with a duckbill valve. Duckbill valves have been used to seal athletic balls, such as footballs, soccer balls, volley balls, etc. Duckbill valve allows an inflating needle to enter to inflate the balls, but seals when the internal pressure is sufficiently high, after the needle is withdrawn. A duckbill valve is disclosed in U.S. Pat. No. 8,002,853, which is reproduced herein as FIGS. 6A-B. Duckbill valve 39 is disposed at the terminal end of vent 41. Duckbill 39 has a neck 39a with opening 39b, which faces the direction of air being vented. When the pressure is low, e.g., when air vents, opening 39b remains open to let air vent as shown in FIG. 6A. When the insufflated liquid, reaches neck 39a with its higher pressure or density, the higher pressure acts on the surface of the neck to close opening 39a to seal vent 41.

Alternatively, duckbill 39 can be manufactured to have small dimensions such that a duckbill 39 can be attached to lumen membrane 36 and to anchor channel/membrane 16 to vent these channels when insufflated or cavity fluids fully fills these channels.

Referring to FIG. 3B, once anchor channel 16 and lumen membrane 36 are filled or when the flapper valve closes, flow sleeve 24 is rotated to an area, preferably a vertical area in this specific embodiment that contains no flow channel to seal anchor channel 16 and lumen membrane 36, e.g., seal area 42 as shown in FIG. 2B. Ingress ports 28 and 32 and egress ports 30 and 34 are sealed by seal area 42 and anchor channel 16 and lumen membrane 36 are filled with cavity fluid 44. Cavity fluid 44 is at substantially the same pressure as the cavity.

An advantage of the present invention is that the pressure in anchor channel 16 can be increased to reduce the probability of cannula 10 being involuntary removed from the incision site while also sealing the cannula to the body. Referring to FIG. 3C, outer compression sleeve 12, which preferably is a solid sleeve, advances distally and compresses anchor channel 16 thereby increasing the pressure inside anchor channel 16, as well as increasing its width or thickness in the horizontal direction as shown in FIGS. 3A-E. With higher internal pressure and larger thickness, anchor channel 16 expands and forms an improved anchor with the skin or tissues surrounding the incision. Preferably, the outer skin of anchor channel 16 may have a certain roughness to enhance the adherence to the skin or tissues.

Another advantage of the present invention is that the pressure in lumen membrane 36 may also be increased to improve the seal around the medical instrument(s) being inserted into cannula 10. Inner compression sleeve 46 also advances distally to compress lumen membrane 36 to increase the pressure inside lumen membrane 36 and its width or thickness in the horizontal direction. This increased thickness, as shown in FIG. 3C, allows the cannula to seal around the medical instruments inserted therein, and seals the lumen of the cannula when instruments are removed.

Once the medical procedure is completed and cannula 10 needs to be removed, the internal pressure and width/thickness of anchor channel 16 should be reduced. Referring to FIGS. 2B and 3D, flow sleeve 24 is rotated until deflating flow channel 40 is aligned with ingress ports 28 and 32, which now act as egress ports. Due to the higher pressure in anchor channel 16 and lumen membrane 36, cavity fluid 44 flows out cannula 10 through deflating flow channel 40 into the cavity. Due to the volume of this exited fluid, the thickness of anchor channel 16 and lumen membrane 36 is reduced and cannula 10 can be readily removed. Or it can be removed simply by loosening the outer compression sleeve.

Figure 3E:
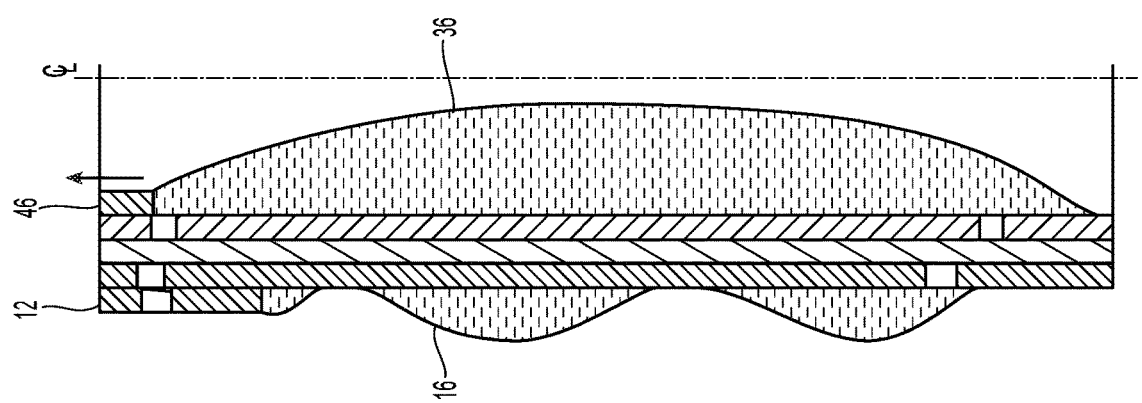
FIG. 3E is the cannula of FIG. 3A showing the lumen membrane being depressurized to allow the medical instrument to be removed or exchanged.
Figure 3D:
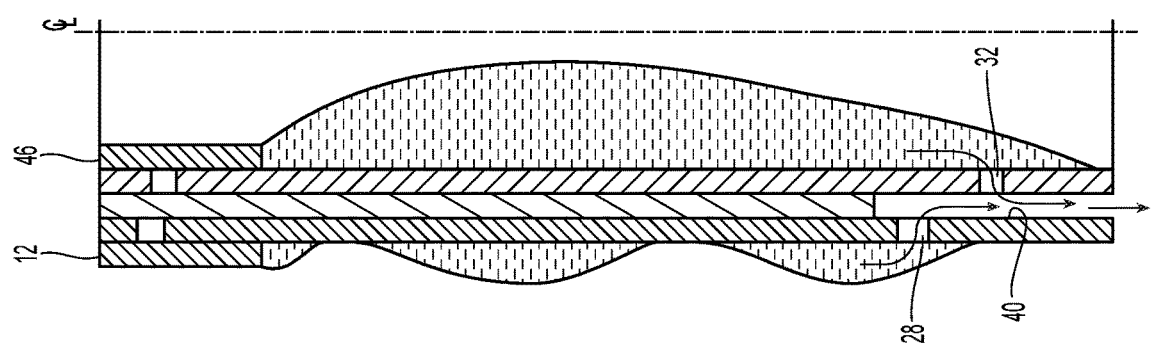
FIG. 3D is the cannula of FIG. 3A showing the lumen membrane and anchor channels being deflated.

In another embodiment, medical instrument(s) can be replaced while cannula 10 remains secured or anchored to the incision site, as illustrated in FIG. 3E. Inner compression sleeve 46 may be moved proximally to relieve the internal pressure of lumen membrane 36 thereby reducing its thickness. This allows a weaker seal around the in situ medical instrument to allow same to be removed, and a different medical instrument can be inserted thereafter. The weaker seal can also be adjusted to allow for various-sized medical instruments. It is noted that inner compression sleeve 46 only has to be moved proximally sufficiently to remove the in situ medical instrument. Inner compression sleeve 46 may be moved distally to close the lumen 26 while another instrument is selected.

Figure 4B:
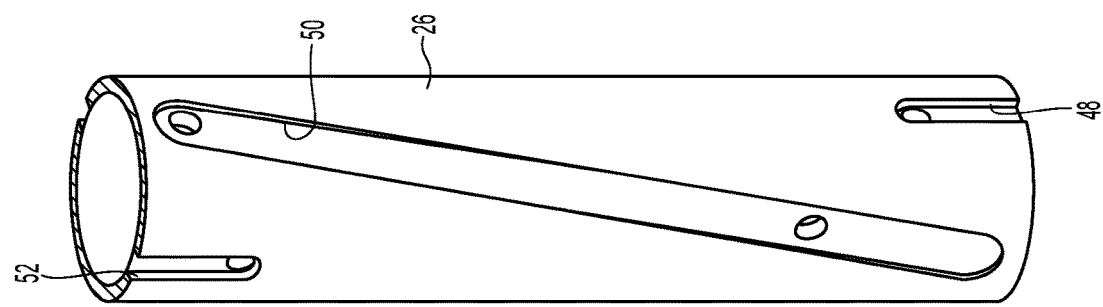
FIG. 4B shows an alternative embodiment where the flow sleeve is omitted and the flow channels are etched onto the surfaces of the lumen or the anchor sleeve.
Figure 4A:
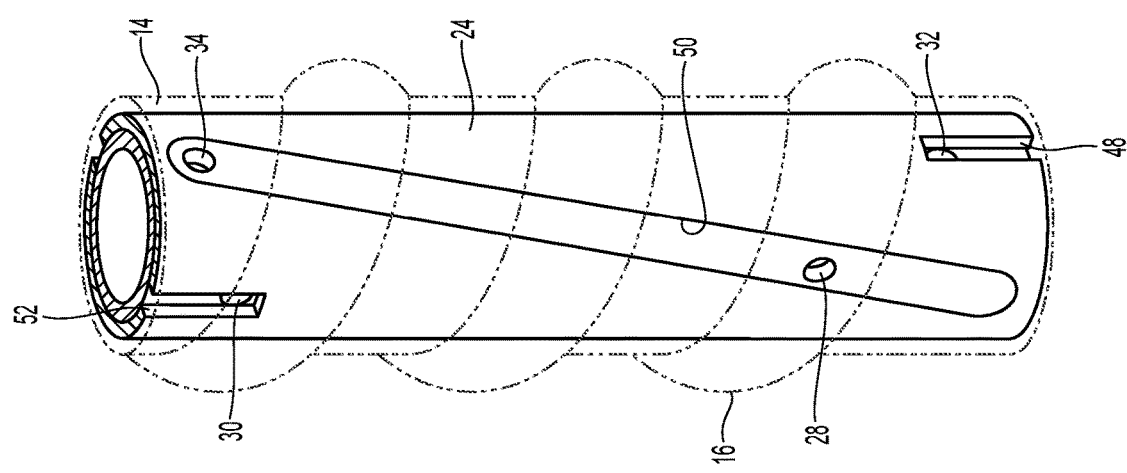
FIG. 4A is a perspective cut-away view of another embodiment of the flow sleeve with selected components omitted for clarity.

In the embodiment described above, preferably the ingress and egress ports, the flow channels on flow sleeve 24 and lumen membrane 36 and anchor channel 16 are sized and dimensioned so that cavity fluid 44 fills both lumen membrane 36 and anchor channel 16 substantially at about the same time. In another embodiment, cavity fluid 44 flows through these two volumes sequentially, i.e., through lumen membrane 36 first and then through anchor channel 16 or vice versa. Referring to FIG. 4A, in this embodiment flow sleeve 14 has inflating flow channel 48 which is in fluid communication with the cavity and ingress port 32 of lumen membrane 36. Connecting flow channel 50 fluidly connects the egress port 34 of lumen membrane 36 to the ingress port 28 of anchor channel 16 (shown in broken line) to direct cavity fluid 44 after it fills up lumen membrane 36 into anchor channel 16. Another inflating flow channel 52 connects egress port 30 (shown in broken line) of anchor channel 16 to the vent/vacuum port.

It is noted that anchor channel 16 can be filled up first. In this version, inflating flow channel 48 is connected ingress port 28; connecting flow channel 50 is connected to egress port 30 and to ingress port 32; and inflating flow channel 52 is connected to egress port 34.

In another embodiment, to minimize the thickness of the cannula, flow sleeve 24 is omitted and flow channels, such as channels 38a, 38b, 40, 48, 50 and/or 52 are etched into either the outer surface of lumen 26 or the inner surface of anchor sleeve 14, or both. It is noted that in this embodiment the flow channels do not cut through the thickness of the lumen or anchor sleeve, but only cut or etch partially through the lumen or anchor sleeve. As shown in FIG. 4B, flow channels 48, 50 and 52 are etched on the outer surface of lumen wall 26. Alternatively, the flow channels can be etched onto the inner surface of anchor sleeve 16.

In yet another embodiment, a vacuum source is provided to pull cavity fluid 44 into lumen membrane 36 and anchor channel 16. An exemplary vacuum source may be a compressed bellows, whose volume when fully expanded would be equal to or greater than the combined volumes of lumen membrane 36 and anchor channel 16. After cannula 10 is inserted into the cavity, the compressed bellows is released to expand. The expansion creates the vacuum force and the bellows' volume is sufficient to pull into lumen membrane 36 and anchor channel 16 a sufficient volume of cavity fluid 44.

In another embodiment, the bellows is initially fully filled with cavity fluid 44 or external fluid. After cannula 10 is inserted into the cavity, the bellows is compressed to inject fluid 44 into lumen membrane 36 and anchor channel 16.

In both embodiments, the bellows can be replaced by an empty syringe as the vacuum source when the plunger is pulled backward, or by a syringe filled with fluid to be injected into the lumen membrane or bellows or anchor channel filling it with fluid. An external valve or a sealing rubber stopper 115 can be deployed so that the syringe can be connected to the cannula and more specifically to the lumen membrane, anchor channel or the bellows.

Figure 5A:
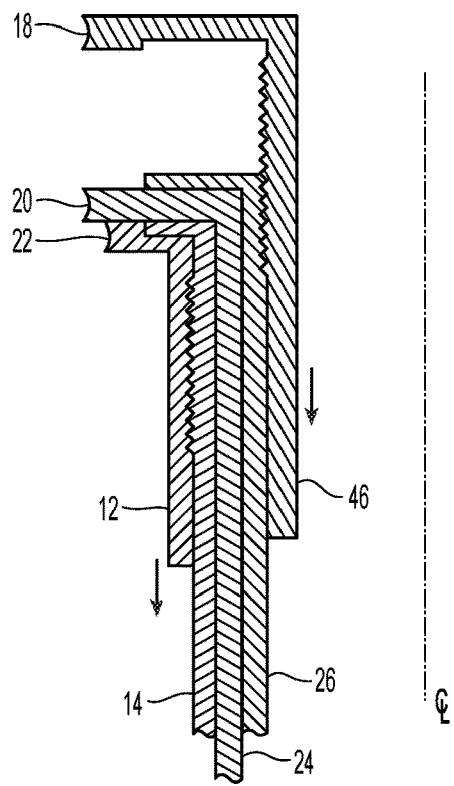
FIG. 5A is a partial cross-sectional view of the concentric sleeves of the inventive cannula and their control dials in a pre-insertion configuration.
Figure 5B:
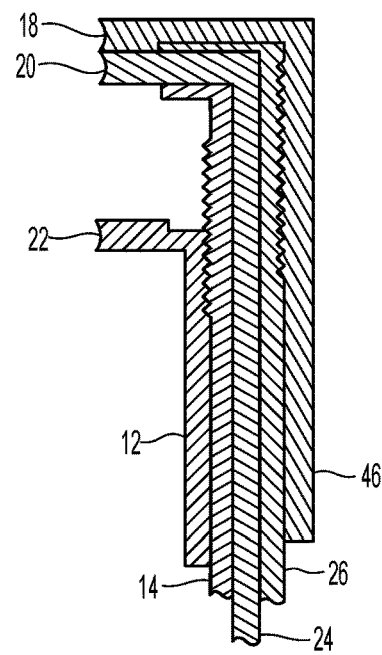
FIG. 5B is the concentric sleeve of FIG. 5A in a post-insertion configuration.

The relative movements of cannula 10's five concentric tubular members are described with reference to FIGS. 1 and 5A-B. The three control dials 18, 20, 22 are connected to the three movable tubular members, i.e., inner compression sleeve 46, flow sleeve 24 and outer compression sleeve 12, respectively. Anchor sleeve 14, which would be in contact with the skin and tissues at the incision site, and lumen 26 are generally stationary when deployed and may be attached to each other at the distal end. In other words, lumen 26 and anchor sleeve 14 may be optionally connected at their distal ends by spot welding or other intermittent attachments so that they are not rotatable relative to each other. Inner compression sleeve 46 is threadedly connected to lumen 26 and in its initial configuration its control dial 18 is in a raised position, as shown in FIG. 5A. Flow sleeve 24 is rotatable relative to lumen 26 and anchor sleeve 14, as discussed above, and can be rotated by its control dial 20. It is noted that flow sleeve 24 does not move translationally with respect to lumen 26 and anchor sleeve 14. Outer compression sleeve 12 is threadedly connected to anchor sleeve 14 and in its initial configuration its control dial 22 may be positioned adjacent to control dial 20, so long as it has room to move distally. Preferably, the outer compression sleeve stays above the skin or the incision site.

After cannula 10 is inserted through the incision site and into the cavity and is filled, in one embodiment control dial 22 is rotated to advance outer compression sleeve in the distal direction, as shown, to compress anchor channel 16, as discussed above. Preferably, after the cannula is secured, control dial 18 is rotated to advance inner compression sleeve 46 in the distal direction to close lumen 26. At this point, cannula 10 would have the configuration shown in FIG. 5B. To reopen lumen 26 to insert a medical instrument, as illustrated in FIG. 3E, control dial 18 is rotated in the opposite direction to advance inner compression sleeve 46 in the proximal direction to open lumen 26.

In the embodiment shown in FIGS. 1-5 and their subparts, the flow controls are accomplished by the relative rotations of the concentric sleeves or tubular members of the cannula. In another embodiment, the flow controls are accomplished by the relative rotations of a manifold connected to the proximal end of the cannula. The manifold preferably comprises a covering layer comprising a plurality of ports and a rotating layer with extended tabs to open or close the ports. The ports are fluidly connected to a number of fixed flow channels defined in the cannula, and the rotating layer rotates relative to the ports on the covering layer to select which flow channels to open or to vent, and which flow channel to close, as described below.

Figure 7:
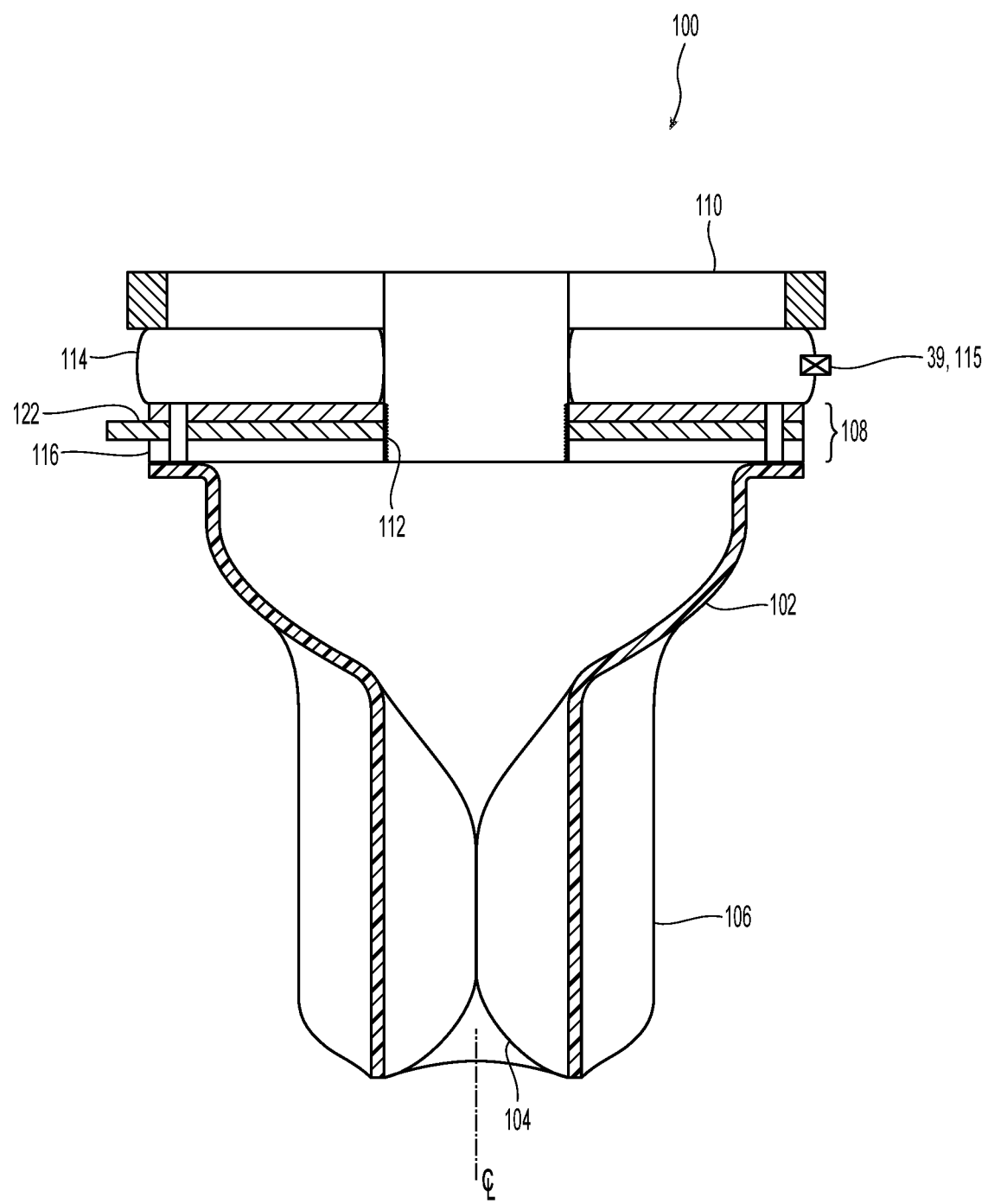
FIG. 7 is a cross-sectional view of another inventive cannula.

Referring to FIG. 7, another inventive surgical cannula 100 is shown. Cannula 100 comprises lumen wall, lumen body or external casing 102 that defines a lumen therewithin, which has inner lumen membrane 104 on its inner surface and outer anchor/seal membrane 106 on its outer surface. Casing 102 comprises a number of internal flow channels, which are described below and omitted in FIG. 7 so that the flow control components on the proximal end of cannula 100 can be more clearly shown. Connected to the proximal end of casing 102 is manifold 108, which may comprise several stacking layers. Rotating cap 110, which has threaded connector 112 is threadedly connected to manifold 108. Sandwiched between rotating cap 110 and manifold 108 is bellows 114. Threaded connector 112 is sized and dimensioned to connect with the threads on manifold 108, as shown. Cap 110 is rotated in one direction toward manifold 108 to squeeze bellows 114 to push fluid inside bellows 114 into lumen membrane 104 to seal the lumen of the cannula and any medical instrument(s) that pass through the lumen, and/or into outer sealing membrane 106 to anchor/seal cannula 100 to the incision site preventing pressurized cavity or insufflated fluid from leaking around the cannula. Cap 110 is rotated in the other direction away from manifold 108 to relieve pressure within bellows 114, so that the cannula can be removed as the outer sealing membrane is depressurized, and/or the medical instrument(s) can be removed or exchanged as the the inner membrane is depressurized and the lumen opened.

Figure 8:
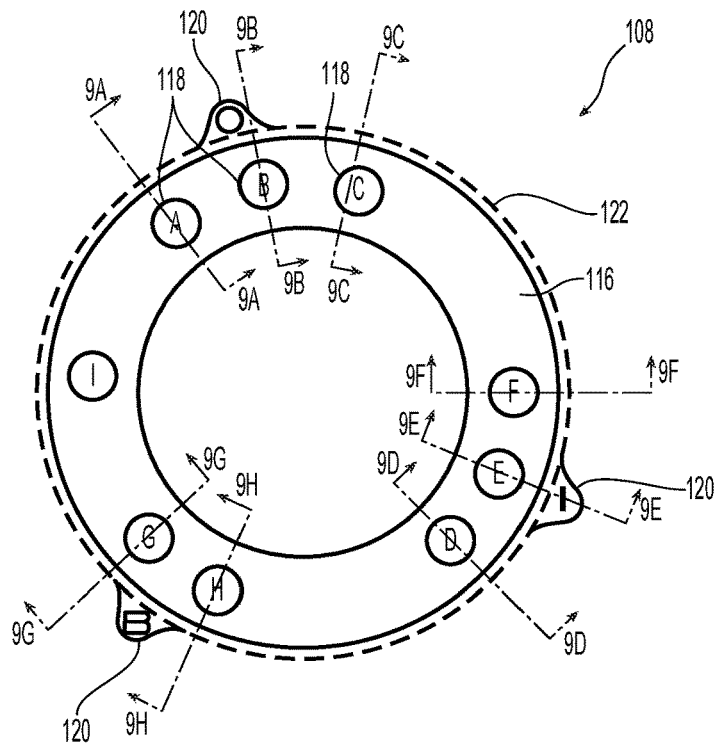
FIG. 8 is a top view of the manifold of the cannula of FIG. 7.

Manifold 108, as best shown in FIG. 8, has a covering layer 116 which comprises a plurality of ports 118. A selected number of ports 118 are connected to the ingress or egress on casing 102. Superimposed on covering layer or port layer 116 is rotating layer 122 with a plurality of tabs 120, which are rotatable to open or close one or more ports 118, as discussed below.

Ports A, B and C are available to fill and compress outer anchor membrane 106. Preferably, port A is fluidly connected to outer anchor membrane 106 to allow fluid to enter the outer anchor membrane; port B is fluidly connected to outer anchor membrane 106 and is fluidly connected to the outer membrane vent, which may vent into bellows 114 described further below; and port C fluidly connects bellows 114 to outer anchor membrane 106 so that outer anchor membrane can be pressurized. When ports A and B are open, outer anchor membrane 106 can be filled with cavity fluid. Tab O can selectively open and close one or more ports A, B or C. The fluidic connections when ports A, B, and C are open are shown in partial cross-sectional views of FIGS. 9A, 9B and 9C, respectively.

Ports D, E and F are available to fill and compress inner lumen membrane 104. Preferably, port D is fluidly connected to inner lumen membrane 104 to allow fluid to enter the inner lumen membrane; port E is fluidly connected to inner lumen membrane 104 and is fluidly connected to the inner membrane vent, which may also vent into bellows 114 described further below; and port F fluidly connects bellows 114 to inner lumen membrane 104 so that inner lumen membrane 104 can be pressurized. When ports D and E are open, inner lumen membrane 104 can be filled with cavity fluid. Tab I can selectively open and close one or more ports D, E or F. The fluidic connections when ports D, E and F when open are shown in partial cross-sectional views of FIGS. 9D, 9E and 9F, respectively.

Ports G and H are available to fill bellows 114. Port G is in fluidic communication with either inner lumen membrane 104 or outer anchor membrane 106 or both during the filling process, and port H is the vent for the bellows. Alternatively or preferably, port G is open to the lumen for the cavity fluid to directly fill bellows 114. The fluidic connections of ports G and H when open are shown in partial cross-sectional views of FIGS. 9G and 9H, respectively. Alternatively, vent ports B and E may be fluidic connected to bellows 114 so that the vent fluid can empty into the bellows allowing the bellows to fill with fluid after the membranes are filled and port G may be omitted. In another embodiment port H can be replaced by an external valve 115 to cannula 100, controlled manually by the surgeon. This manual valve is opened by the surgeon upon insertion of the cannula in the incision site to allow air to pass out of the cannula while it is filling with insufflated fluid. The manual valve is then closed by the surgeon. Alternatively, all three vents B, E, and H can be connected to this external valve 115.

Port I in one embodiment when open allows the cavity fluid or insufflated fluid to enter vent manifold 108 and is preferably connected to port A of outer anchor membrane and port D of inner lumen membrane, so that cavity fluid enters port I and moves to ports A and D. Ports B and E are also open so that cavity fluid may displace air in the membranes to escape either externally or into bellows 114 first and then externally out of the cannula. Alternatively, the cannula can be pre-filled with fluid from a syringe connected to the external port. Preferably, port I is also connected to port G to allow cavity fluid to enter bellows 114 and port H is open to vent. Preferably, a duckbill valve 39 is positioned at the terminal end of each vent 41(except the external vent of the bellows), so that each vent closes when cavity fluid reaches the duckbill and acts as a one-way valve vent or release valve. In one alternative, ports B, E and H are fluidly connected together and to a single vent/duckbill valve, which may be opened manually to allow air to escape the system. When all the vents are connected to a single manual external valve 115 that can be opened and closed by the surgeon, as discussed above, duckbill valve(s) can be omitted. Minimizing the number of valves would simplify manufacturing and would reduce costs.

Figure 10:
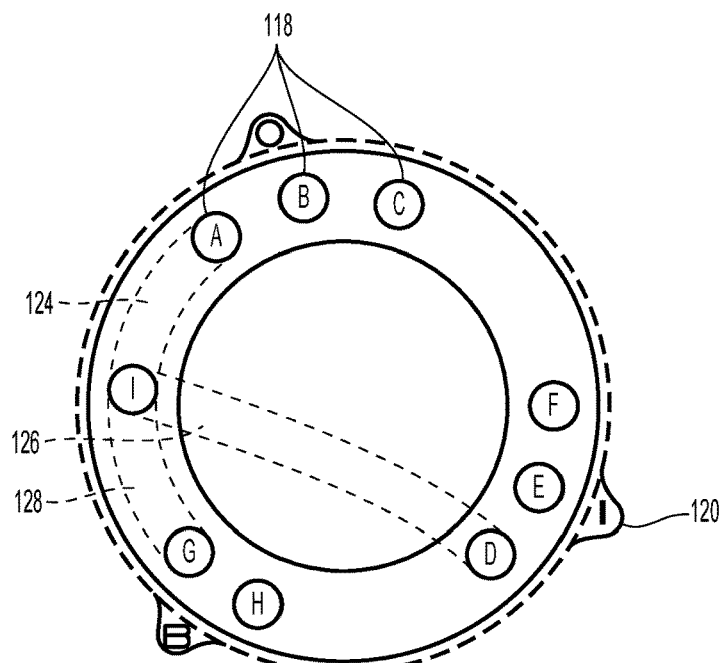
FIG. 10 is a top view of the manifold of FIG. 8 with flow channels on the rotating layer.

Referring to FIG. 10, an exemplary rotating layer 122 with tabs O (Outer), I (Inner) and B (Bellows) shown in broken line overlaps covering layer 116 shown in solid lines with ports A-I. Port I, which is open to the lumen inside casing 102 to receive cavity fluid. Port I is connected to port A via flow channel 124, to port D via flow channel 126, and to port G via flow channel 128. In this embodiment, each tab O/I/B is individually controlled to open or close ports A-H. Port I can be opened or closed by tab B, I or O.

The flow channels shown in FIGS. 9A-H can be molded into the body or casing 102 of cannula 100, or through covering or port layer. Alternatively, the lumen can be constructed out of two layers with the flow channels being etched into either one or both of the layers, as discussed above. Alternatively, the flow tubes can be laid on the surface of casing 102, such as running on the surface of the inner wall. Preferably, casing 102 is manufactured by 3-D printing, which can produce any product, including those with complex geometry. The walls of casing or body 102 with the internal flow channels shown in FIGS. 9A-9H can be printed with a polymer, such as a thermoplastic polymer.

Figure 11A:
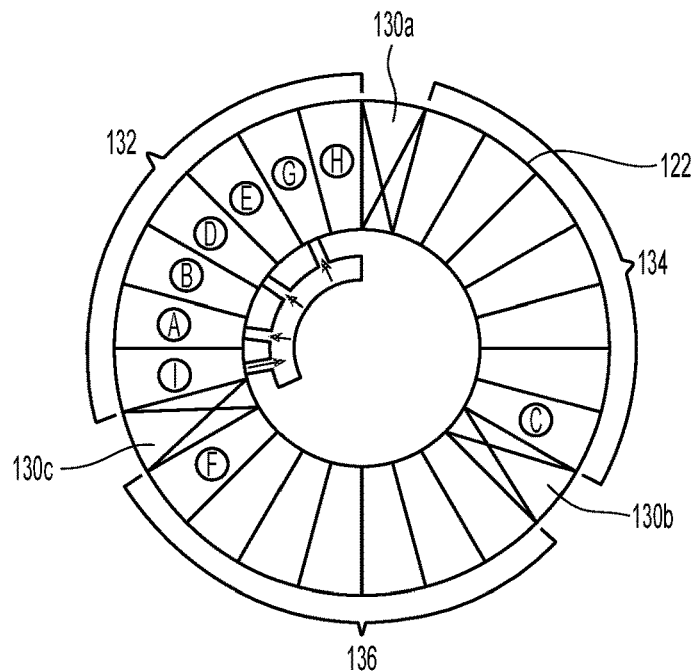
FIGS. 11A-B are top views of another covering layer and rotating layer of the manifold.
Figure 11B:
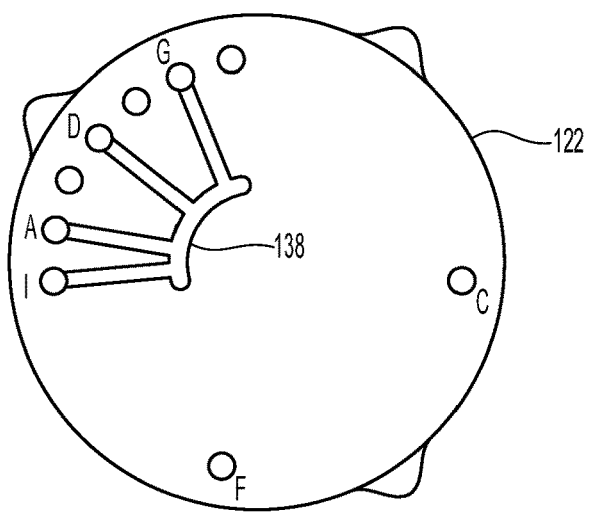

Another exemplary rotating layer 122 and covering layer 116 are shown in FIGS. 11A-B, wherein the various flow controls are selected by turning rotating layer 122 instead of the various tabs individually. As shown, covering layer 116 is divided into a number of segments, which preferably may have equal size. In this example, twenty-four segments are shown; however, any number of segments greater than the number of ports can be used. In this example, the ports are arranged on covering layer 116 such that the inlet port I is adjacent to the pairs of inlet and vent ports, i.e., inlet port A is adjacent to vent port B for outer anchoring membrane 106; inlet port D is adjacent to vent port E for inner lumen membrane 104; and inlet port G is adjacent to vent port H. Inlet ports I, A, D and G are connected together, so that cavity fluid or insufflated fluid or external fluid entering manifold 108 at port I can simultaneously enter outer anchoring membrane 106, inner lumen membrane 104 and bellows 114 via inlet ports A, D and G, respectively. Air is vented externally.

After the membranes and bellows are filled and the vent(s)/duckbill(s) or the manual external valve 115 are closed or after the rotating layer is turned to close the ports, the cavity fluid can be turned "OFF" by simply turning rotating layer 122 a distance equal one segment, e.g., in the counter-clockwise direction, so that inlet port I faces end segment 130 and is closed. Inlet ports A, D and G would face holes for vent ports B, D and H, which are already closed by duckbill(s) 39 or external vent valve. Unless port I on covering layer 116 is positioned across from its corresponding hole on rotating layer 122, port I is closed. Hence, there are (N−1) segments where port I is closed.

As best shown in FIG. 11A, the segments are divided into three groups separated by end segments 130*a*, 130*b*, and 130*c*. Group 132 comprises ports I, A, B, D, E, G and H described above. Group 134 comprises port C, which fluidly connects bellows 114 to outer anchor membrane 106. Group 136 comprises port F, which fluidly connects bellows 114 to inner lumen membrane 104.

To access port C, rotating layer 122 is rotated until port I is opposite to first end segment 130a. All ports are closed except port C. Cap 110 is rotated in one direction, e.g., clockwise, to compress bellows 114 to pressurize outer anchor membrane 106 to anchor/seal cannula 100, and is rotated in the other direction to decompress bellows 104 to release pressure in outer membrane 106 to remove or reposition cannula 100.

To access port F, rotating layer 122 is further rotated until port I is opposite to second end segment 130b. All ports are closed except port F. Cap 110 is rotated in one direction, e.g., clockwise, to compress bellows 114 to pressurize inner lumen membrane 104 to seal the lumen, or to seal the medical instrument(s) within the lumen, and is rotated in the other direction to decompress bellows 114 to release pressure in inner lumen membrane 104 to unseal the lumen, to allow the insertion and removal of medical instrument(s).

Hence, advantageously the pressures in outer anchor membrane 106 and in inner lumen membrane 104 can be controlled individually or separately. Furthermore, cap 110 and bellows 114 are used to pressurize both outer anchor membrane 106 and inner lumen membrane 104. The volume of bellows 114 should be sufficient to provide fluid, preferably liquid, to pressurize both membranes.

The rotating layer 122 that corresponds to the covering layer 116 shown in FIG. 11A is shown in FIG. 11B. Flow channel 138 connects the holes that correspond to ports I, A, D and G. The holes adjacent to these ports correspond to the vent ports, and the holes that correspond to ports C and F are also shown.

Additionally, manifold 108 can be designed so that there is a setting to pressurize both outer anchor membrane 106 and inner lumen membrane 104 at the same time, which can be advantageous during the insertion of cannula 100 into the incision site. Covering layer 116 can be divided into four groups of segments separated by four end segments 130. In this non-limiting example, covering layer 116 has 32 segments divided into four groups and four end segments 130. The fourth or additional group has ports C and F, which allow cap 110 to squeeze bellows 114 to pressurize both membranes at the same time.

In yet another embodiment, a simplified cannula similar to the embodiment shown in FIGS. 7-11 is provided. In this embodiment, bellows 114 is prefilled with a liquid, such as a saline solution, either when manufactured or by the surgeon/physician before or after insertion into the incision site. This embodiment can be illustrated with FIGS. 7, 9C and 9F. This version of cannula 100 can be represented by FIG. 7. Bellows 114 has a flow channel to establish a fluid communication with outer anchor membrane 106, as illustrated in FIG. 9C and bellows 114 has another flow channel to establish a fluid communication with optional inner lumen membrane, as illustrated in FIG. 9F. Bellows 114 may have an external valve 115, such as a duckbill valve discussed and shown above or any conventional valve that can open and close, to allow the insertion of a needle, a syringe, or other means to fill of the bellows. Valve or stopper 115 can be a refilling port for bellows 114.

To inject liquid into one or both of the membranes rotating cap 110 is rotated to squeeze bellows 114. Preferably, rotating cap 110 has a pawl and toothed cogwheel retention system so that the rotating cap does not unintentionally rotate in the reverse direction. Such pawl and toothed system is well known and is described in U.S. Pat. No. 2,268,243, which is incorporated herein by reference in its entirety. In one version, there is no flow restrictor or flow selector in the flow channel(s) because the pawl and toothed system can maintain the pressure in the membranes after inflation. In another version, a rotating layer, such as layer 122, or tabs 120 can be included to restrict the flow in the flow channels shown in FIGS. 9C and 9F. Preferably, the inflated pressure is higher than or equal to the pressure of the cavity fluid.

An alternative to the rotating cap 110 with or without the pawl and toothed cogwheel retention system is a pushbutton plunger within a cap, similar to those in pushbutton pens and writing instruments. The pushbutton would locate inside a cap. When pushed downward relative to the cap the pushbutton rotates a ratchet, which engages and disengages spaced apart teeth on the inner wall of the cap. Hence, as first push of the pushbutton may advance the cap downward to push on bellows 114 to push fluid into the outer anchor membrane and optionally into the inner lumen membrane. A second push of the pushbutton may retract the cap upward to pull on bellows 114 to pull fluid from the outer anchor membrane and optionally from the inner lumen membrane to withdraw cannula 100 or the medical instruments inserted therein. Such pushbutton plunger and ratchet mechanism is described in U.S. Pat. Nos. 3,288,155 and 3,120,837, which are incorporated herein by reference in their entireties.

Alternatively, in the pushbutton plunger embodiment the downward pushes of the pushbutton continue to push the cap downward to push on bellows 114 to push fluid into the outer anchor membrane and optionally into the inner lumen membrane, or to increase the pressure in these membranes. In other words, the pushbutton plunger is a piston, similar to those described below. When the desired pressure is reached a locking mechanism can be employed to lock the pushbutton in place, maintaining the pressure. Alternatively, the fluidic communication with the membranes is cut off for example by manifold 108 and rotating layer 122 as described above to keep the membrane pressurized. The locking mechanism is released to release the pressure, or the fluidic communication is re-opened.

In yet another embodiment as best shown in FIG. 12, in this embodiment an internal bellows 140 is inserted inside element 114, which is described in the other embodiment as a fluid containing bellows. Internal bellows is connected to a pump 142 via a valve 144. Pump 142 can pump a fluid such as air into internal bellows 140 to expand the internal bellows. This pushes fluid contained in element 114 into the outer anchor membrane 106 and optionally into lumen membrane 104. Pump 142 can be a simple hand pump or blister pump or various electrical pumps or medical pumps. Rotating cap 110 can be omitted in this embodiment, and element 114 can be substantially rigid, or can be flexible or elastic, e.g., an outer bellows. If element 114 is an outer bellows, when inner bellows 140 is inflated the fluid in element 114 is pressurized by both internal bellows 140 and elastic outer bellows 114 thereby increasing the pressure in the anchor and lumen membranes and in outer bellows 114 without using a high capacity pump 142.

The embodiment of FIG. 12 shows that the bellows on the inventive cannula can be both an internal bellows inside an outer container (which can be another bellows) and does not contain fluid to inflate the outer anchor membrane and optionally lumen membrane, and a bellows shown in FIG. 7 that does contain fluid to inflate the outer anchor membrane and optionally lumen membrane. The present invention includes both configurations and the term activating the bellows includes both compressing the bellows to push fluid into the membrane(s) and expanding the bellows, e.g., the internal bellows to push fluid into the membrane(s).

The optional inner lumen membrane 36, 104 and outer anchor membrane 16, 106 are in one embodiment made from elastic materials, such as those in surgical balloons, so that a positive pressure is needed to inflate the membranes and that these membranes can squeeze fluid/liquid therefrom when the membranes are open to vent or to bellows 114 to facilitate the removal of cannula 10, 100.

Another embodiment of the inventive surgical cannula is illustrated in FIGS. 13 and 14 and their subparts. Cannula 150 comprises a lumen wall 152, a flow piston 154 with distal sealing member 155 and outer casing 156 with an outer anchor membrane 158 attached to the outside thereof and with proximal sealing member 157. A diaphragm covering the lumen is preferred included to cover the lumen, and an optional inner or lumen membrane similar to those discussed above can also be used to cover the lumen. Lumen wall 152 abuts flow piston 154 and preferably these two components form a seal with each other, until flow ports located on each member align with each other, as described below. Outer casing 156 is positioned spaced apart from flow piston 154 and forms an annular or donut or horseshoe shaped fluid chamber 160 defined in the space between flow piston 154 and outer casing 156, and between distal sealing member 155 and proximal sealing member 157.

Cannula 150 has certain similarities to a syringe, but with annular fluid chamber 160 and the plurality of ports. As best shown in FIG. 13A, which shows the configuration where fluid enters cannula 150 and its outer membrane 158, and FIGS. 14A-C. Lumen wall 152 has at least one, or more, lumen ports 162, and flow piston 154 has corresponding piston ports 164. When lumen ports 162 align with piston ports 164, a fluid communication is established between the lumen defined by lumen wall 152 and fluid chamber 160. Outer casing 156 has at least one membrane port 166 to establish fluid communication between outer anchor membrane 158 and fluid chamber 160. Outer casing may also have optional first vent 168 and second vent 170, described below.

Fluid, preferably insufflated fluid in the body cavity enters cannula 150 when its vent(s) is opened. Alternatively, cannula 150 may be prefilled with another fluid, such as medical grade saline solution. Fluid is pushed into the lumen space within lumen wall 152 through the alignment of lumen ports 162 and piston ports 164, as shown in FIG. 13A, into and filling fluid chamber 160. Fluid also flows into outer anchor membrane 158 through membrane ports 166. Entrapped gas or air is vented from the space in outer membrane 158 to fluid chamber 160 through first vent 168 and from fluid chamber 160 to the outside through second vent 170 to outside of cannula. In one variation, a duckbill valve 39 is disposed in one or both vents 168, 170 to minimize or prevent liquid from exiting cannula 150, as discussed above in reference with FIGS. 6A-B.

Figure 13B:
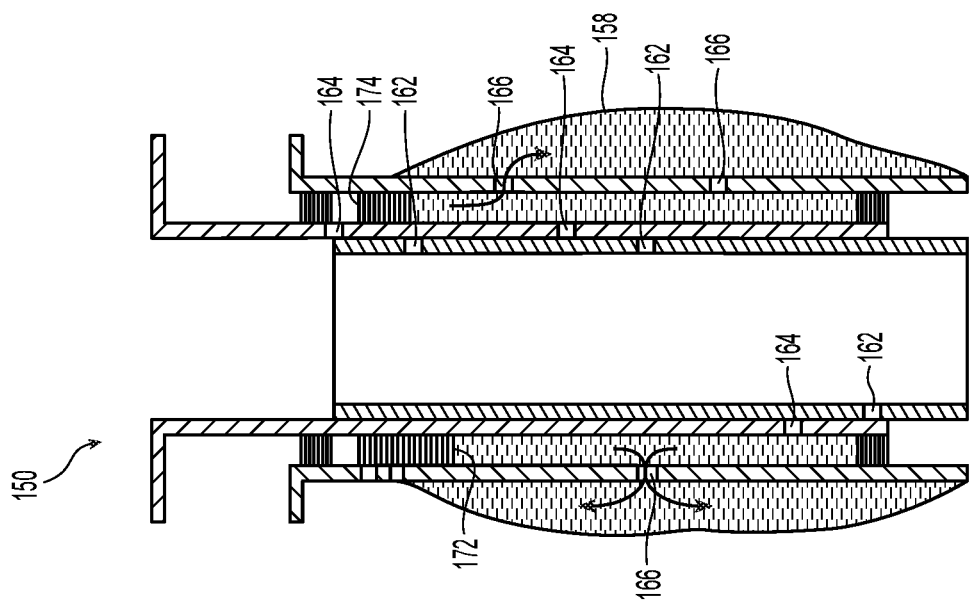
FIGS. 13A-B are cross-sectional views of another embodiment of the cannula of the present invention.
Figure 13A:
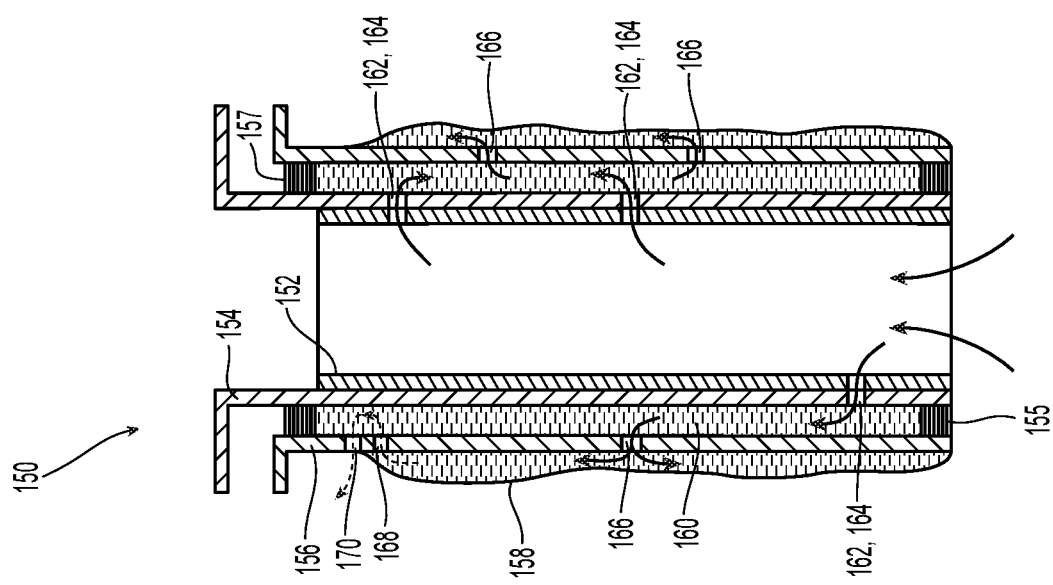

Once outer anchor membrane 158 is at least partially filled and fluid chamber 160 is at least partially filled, to pressurize outer anchor membrane 158 the fluid communication between fluid chamber 160 and the lumen is terminated by misaligning lumen ports 162 and piston ports 164, as best illustrated in FIG. 13B. The misalignment can be accomplished by moving flow piston 154 relative to lumen wall 152 either by relative rotation or by proximal movement of flow piston 154 relative to lumen wall 152, or by both. With at least second vent 170 closed, for example by a normally closed valve 169, shown in FIGS. 13C and 13D and discussed below, disposed in second vent 170, fluid chamber 160 is only fluidically connected to outer anchor membrane 158, and a reduction in volume of fluid chamber 160 would cause an increase in volume and/or pressure within outer anchor membrane 158 to secure cannula 150 to the incision site. This is accomplished by pulling or moving flow piston 154 proximally. Distal sealing member 155 is moved along with flow piston 154, while proximal sealing member 157 being attached to outer casing 156 remains in place. This reduction volume within fluid chamber 160 forces fluid into outer anchor membrane 158 through membrane ports 166.

In another version, flow piston 154 can move distally, i.e., in the opposite direction, if distal sealing member 155 is stationary and is attached to outer casing 156 and proximal sealing member 157 is attached to flow piston 154 and is movable therewith, so long as second vent 170 is sealed, as discussed below in connection with piston sealing member 172 or normally closed valve 169. In this version, preferably flow piston 154 extends further above outer casing 156 to provide a sufficient stroke length, and as flow piston 154 extends distally it enters the body cavity.

Figure 13C:
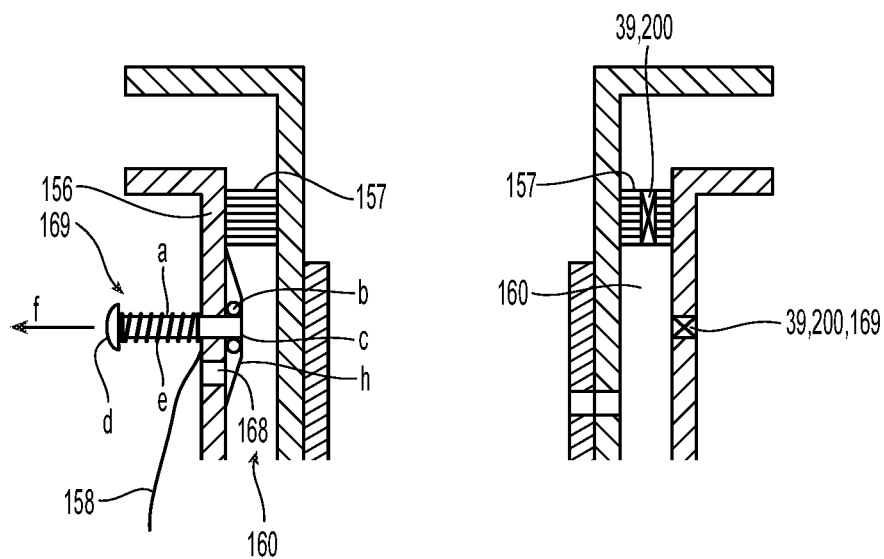
FIGS. 13C-D are cross-sectional views of another embodiment of the cannula of the present invention showing among other things a normally closed valve.
Figure 13D:
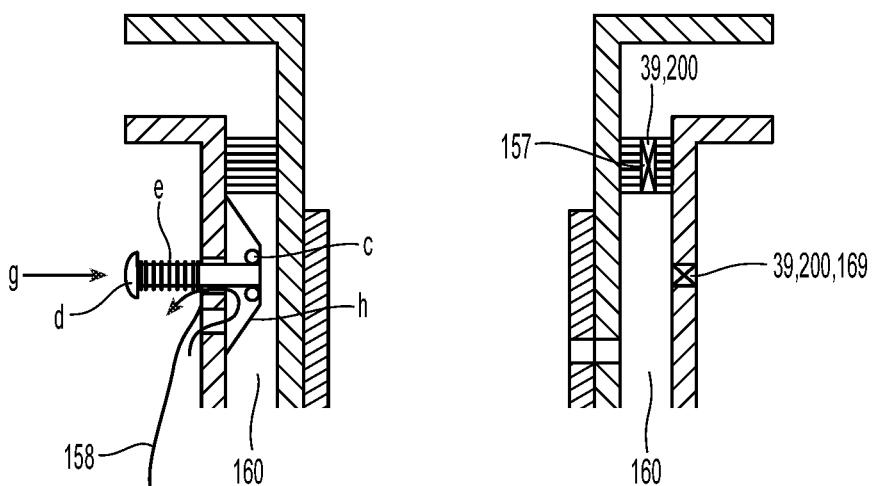
Figure 14C:
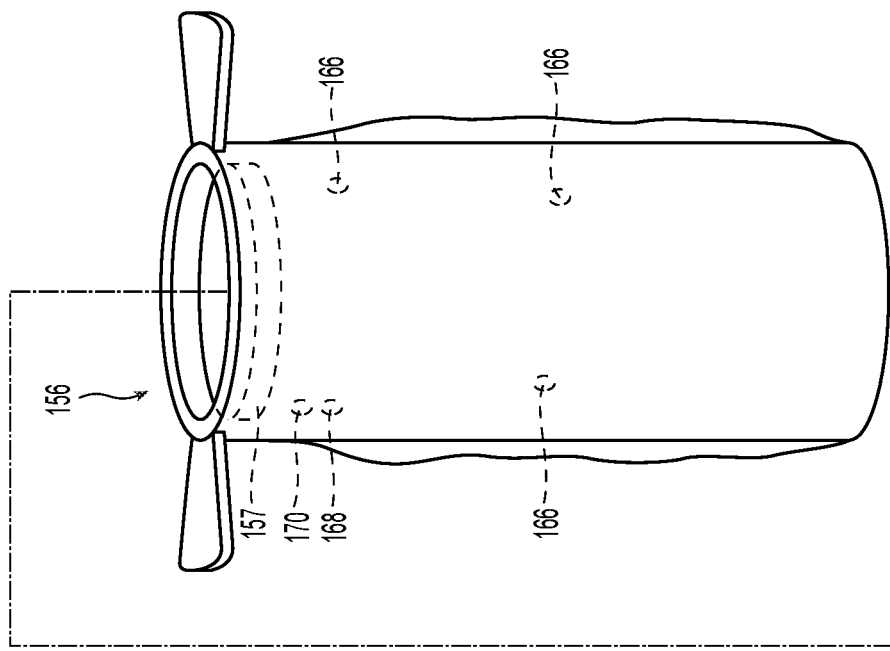
FIGS. 14A-C are perspective views of the components of the embodiment illustrated in FIGS. 13A-B.
Figure 14B:
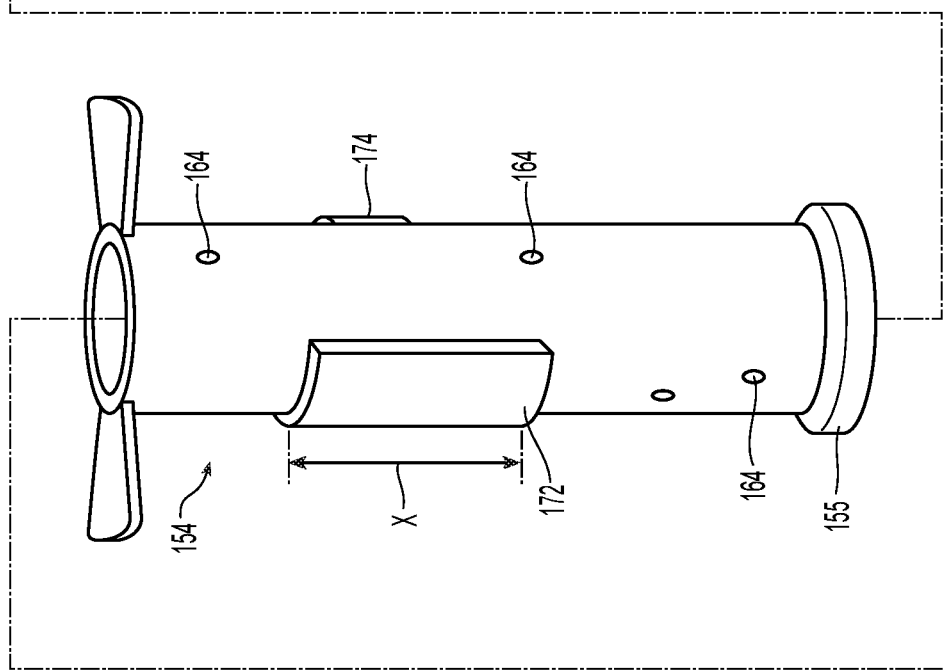
Figure 14A:
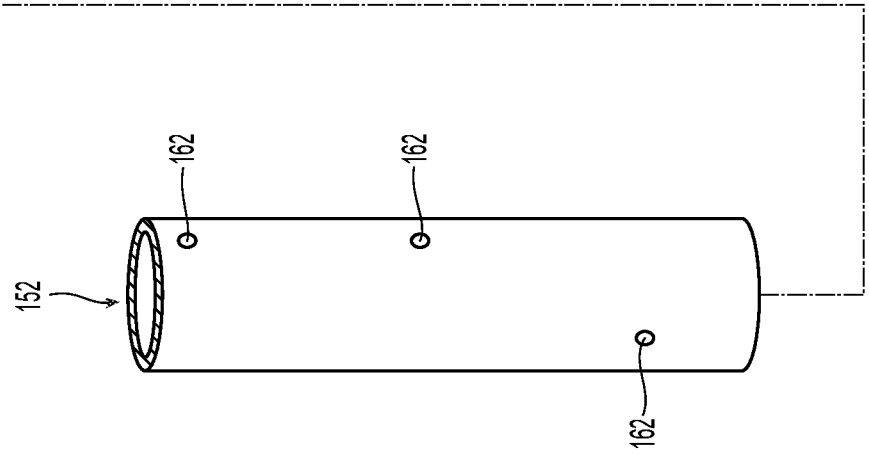

Referring to FIGS. 13C-D, normally closed valve 169, which can be activated by the user/surgeon and preferably disposed in second vent 170, comprises a rod (a), which passes through vent 170, with an inner end (b) sized and dimensioned hold a sealing member such as O-ring (c). Opposite to inner end (b) is outer head (d). Disposed between head (d) and outer casing 156 is compressed spring (e). Spring (e) biases head (d) and valve 169 in the direction (f) to pull O-ring (e) toward outer casing 156 to close valve 169 to seal vent 170. To open valve 169 and therefore second vent 170, the user presses outer head (d) in direction (g) to push inner end (b) and O-ring (c) away from outer casing 156, to open valve 169 to vent air/gas from fluid chamber 160 during the filling stage, and optionally to release fluid/insufflated liquid from outer membrane 158 in order to remove the cannula. Optionally, a flexible membrane and preferably elastomeric membrane (h) is provided to connect first and second vents 168, 170 and preferably to isolate these vents from the fluid/flow chamber. Membrane (h) allows the venting of the outer anchor membrane without establishing a fluidic connection between the outer anchor membrane and the fluid/flow chamber.

As discussed and used herein, valve 169 may also include vents 168 and 170, as well as membrane (h), as a valve to vent the outer membrane.

In another variation, an optional vent sealing member 172 is attached to the outer surface of flow piston 154. When flow piston is pulled proximally, vent sealing member 172 is moved to block one or both first and second vents 168, 170. Preferably vent sealing member 172 has a length X of sufficient length to cover vents 168, 170 during the pressurization of outer anchor membrane 158. Optionally, a counter-balance member 174 is provided on the opposite side thereof to assist in the centering of flow piston 154, and to provide a pressure on vents 168, 170. Vent sealing member 172 may be provided in addition to duckbill valve(s) 39 in vents 168 and/or 170, or in place of the duckbill(s).

One advantage of this embodiment is that in the event that the tissues surrounding the incision site relax during the procedure, additional pressure can be applied to outer anchor member 158 by additionally moving flow piston 154 proximally to further reduce the volume of fluid chamber 160.

Releasing the pressure or reducing the volume of outer anchor membrane 158 can be accomplished by pushing flow piston 154 distally to increase the volume of fluid chamber 160. Further reduction in pressure/volume can be accomplished by realigning lumen ports 162 to piston ports 164 to allow fluid to exit the cannula into the lumen. Alternatively, the volume and/or pressure in outer anchor membrane 158 can be decreased by further pulling flow piston 154 proximally until the lowest or most distal membrane port 166 is below distal sealing member 155, and the fluid within outer anchor membrane can exit into the body cavity.

To maintain cannula 150 in the configuration illustrated in FIG. 13B, i.e., to maintain pressure in outer anchor membrane 158 to secure the cannula to the incision site, a rotating latch 176, as shown in FIGS. 15A-B, is pivotally attached to either the flange of flow piston 154 or the flange of outer casing 156. As shown, rotating latch 176 has a serrated edge or notches that can hold or grip the other flange. Latch 176 is rotated outward and then flow piston 154 is moved proximally to a desired height. Thereafter, latch 176 is rotated back to hold the other flange to maintain this configuration.

Another rotating latch 178 is illustrated in FIG. 16A-B. In this variation, the serrations or notches are located on the body of flow piston 154. Latch 178 as shown in FIG. 16A is attached to the flange of outer casing 156 and as outer casing 156 is rotated relative to flow piston 154, latch 178 disengages from the notches or serrations. Flow piston 154 is then moved proximally to a desired height. Thereafter, outer casing 156 is rotated in the opposite direction so that latch 178 re-engages the notches or serrations to maintain this height.

Figure 6B:
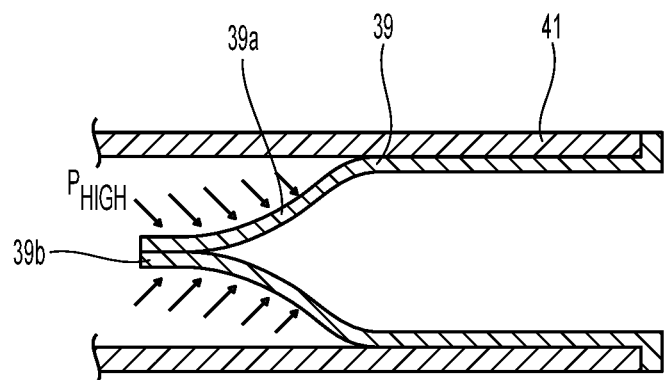

In an alternative embodiment, proximal sealing member 157 that seals the top side of fluid chamber 160 has a one-way valve, such as duckbill 39 shown in FIGS. 6A-B or flapper valve 200 shown in FIG. 19 below, positioned therein such that air is allowed into fluid chamber 160, as illustrated in FIG. 13C-D. Alternatively, such one-way valve can be placed on the outer casing, preferably near the proximal end of fluid chamber 160 and above the incision site. As shown in FIG. 13B, as piston 154 is raised to pressurize outer membrane 158 the elevation of the top of piston 154 may be relatively high relative to the top of outer casing 156. This may cause an ergonomic issue for the surgeons, since the top of the cannula may be too high relative to the patients' skin. Incorporating a one-way valve as illustrated in FIGS. 13C-D allows piston 154 to be pushed downward or distally to lower the elevation of the top of the piston without withdrawing fluid from outer membrane 158. Another advantage of this embodiment is that if additional pressure is required in outer membrane 158, piston 154 can be raised or pulled proximally to push more fluid into outer membrane as illustrated in FIG. 13B. Although air is now inside fluid chamber 160, air is only slightly compressible in this situation and additional pressurization of outer membrane 158 is possible. Alternatively, normally closed valve 169, described above, can be used instead of a one-way valve. The surgeons may manually open valve 169 to allow air to enter fluid chamber 160 when pressing down piston 154.

Optionally, a one-way valve, such as duckbill valve 39 or flapper valve 200 shown in FIG. 19 below, is placed within one or more port, such as lumen port 162, piston port 164 or membrane port 166, to allow one-way flow, as described above and illustrated in FIG. 13A.

Cannula 150 is designed such that insufflated fluid flows into the cannula when the cannula is vented, e.g., at second vent 170, and flow piston 154 is moved proximally or distally to pressurize at least the outer anchor membrane 158 when second vent 170 is sealed. Other inventive cannulas, such as cannulas 180 and 230 described below actively pump insufflated fluid into the internal fluid chamber and then pump the insufflated fluid from the internal fluid chamber into the outer anchor membrane and/or the optional lumen membrane. Venting is optional in cannulas 180 and 230, since any residual air/gas can be used to fill and pressurize the membrane. Furthermore, the membrane can be made from an elastomeric material such that they can be slightly stretched and be positioned adjacent to the outer casing or to the lumen wall to minimize the amount of initial gas/air within the cannulas. The internal fluid chamber may also have low or substantially zero air space therewithin before the first use to minimize the amount of air/gas within the cannulas.

Figure 17A:
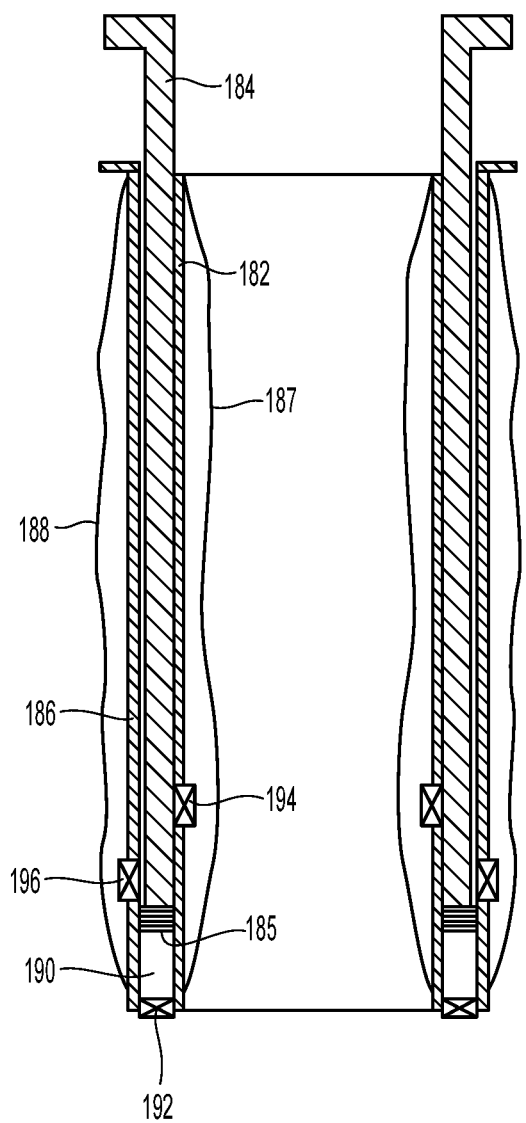
FIGS. 17A-C are cross-sectional views of another embodiment of the cannula of the present invention.

Another embodiment of the inventive surgical cannula is illustrated in FIGS. 17 and 18 and their subparts. Cannula 180 comprises a lumen wall 182, a flow piston 184 with distal sealing member 185 and outer casing 186 with an outer anchor membrane 188 attached to the outside thereof and with optional lumen membrane 187 attached to the inside of lumen wall 182. Lumen wall 182, outer casing 186 and distal sealing member 185 form a fluid chamber or reservoir 190. Fluid chamber 190 has at least one one-way reservoir valve 192 disposed at the distal end thereof and is in fluid communication with the body cavity. Lumen wall 182 has at least one optional one-way lumen valve 194 and outer casing 186 has at least one one-way casing valve 196. The flow directions of these one-way valves are described below.

Similar to cannula 150, cannula 180 is similar to a syringe having an annular fluid chamber/reservoir, i.e., the space between lumen wall 182 and outer casing 186, and a piston with a distal sealing member. As discussed below, the annular fluid chamber may have a horseshoe shaped with a vertical drainage channel, discussed below.

Figure 17B:
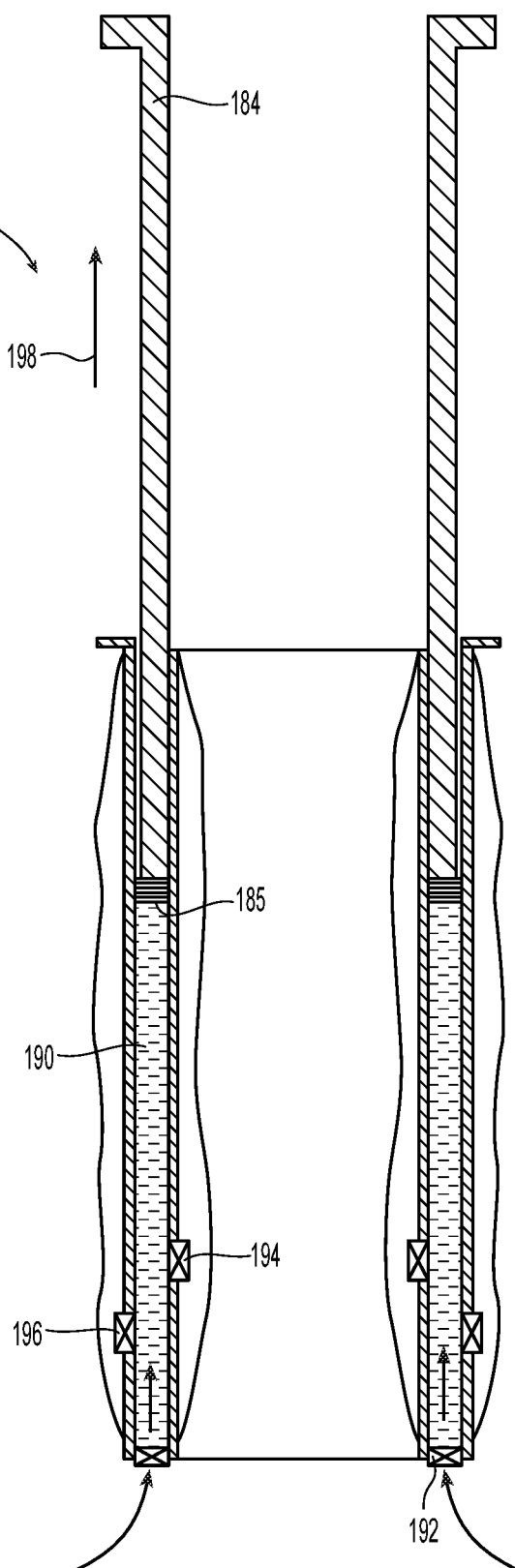

After the distal end of cannula 180 is inserted through an incision site into a body cavity, similar to the other inventive cannula described above, a user/surgeon primes the cannula by pulling up on flow piston 184 along arrow 198, as shown in FIG. 17B. One-way valve 192 only allows fluid/liquid to flow from the body cavity into flow chamber 190 as shown filling flow chamber 190. One-way valves 194 and 196 only allow fluid/liquid to flow from flow chamber 190 out to outer membrane 188 and lumen membrane 187 under a positive pressure within flow chamber 190. Pulling the flow piston upward creates a negative pressure or partial vacuum in flow chamber 190, and the fluid in the body cavity being drawn into flow chamber 190 would not flow into the membranes.

Figure 19:
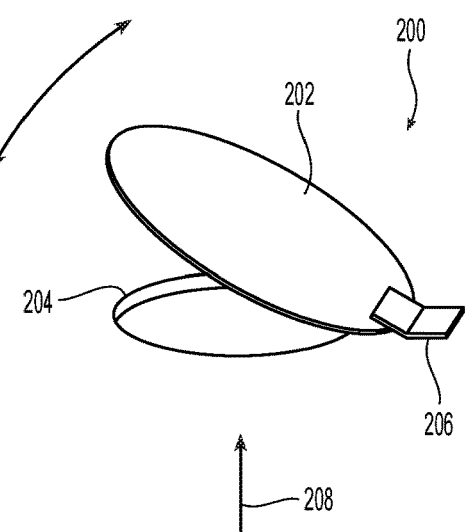
FIG. 19 is a perspective view of another exemplary one-way valve suitable for the various embodiments of the present invention.

A suitable one-way valve includes, but is not limited to, a flapper valve 200, as shown in FIG. 19. Flapper valve 200 comprises a flapper sealing member 202 which is larger than valve opening 204 so that flapper 202 may seal valve opening 204. Flapper 202 is attached to a valve seat by a live joint 206. In one example, flapper 202 is made from an elastomeric material and is heat sealed to the valve seat to form the live joint. The live joint 206 exerts a biasing force tending to bias flapper 202 to cover hole 204 to seal one-way valve 202. A positive pressure in the direction of arrow 208 could overcome the biasing force from live joint 206 to open the valve to allow fluid to flow in the direction of arrow 208. Once the positive pressure is withdrawn, the biasing force closes the valve.

Another suitable one-way valve is duckbill valve 39, discussed above and illustrated in FIGS. 6A-B.

After flow chamber 190 is primed, flow piston 184 is pushed downward in the direction of arrow 210, the positive pressure in flow chamber 190 would close one-way valve 192 for example by pressing down on flapper 202 of flapper valve 220 or on the outside of nozzle 39b of duckbill 39, and at the same time opens optional one-way lumen valve 194 if lumen membrane 187 is present and opens one-way casing valve 196 to fill outer membrane 188 to anchor cannula 180 to the incision site. In one option, the volume of flow chamber 190 is sized and dimensioned to fill one or both of membranes 187, 188. In another option, to reduce the size of cannula 180 and the volume of flow chamber 190, the user/surgeon may repeat the priming step (pulling up flow piston 184 in direction 198) and the downward step (pushing down flow piston 184 in direction 210) until the membranes are filled and pressurized. During the surgical procedure, if additional pressure is needed, flow piston 184 may be pushed down further and/or pulled up to add more fluid into flow chamber 190 and then pushed down.

Advantageously, the pressures within membranes 187 and 188 are self-correcting. For example, if the pressure in lumen membrane 187 is higher than that in outer membrane 188, additional fluid being pushed by flow piston 184 would seek a path of lesser resistance and flow into outer membrane 188, and vice versa. Hence, if one membrane is fully pressurized and the other one is not, continuing pushing on flow piston would pressurize the lesser pressurized membrane.

Alternatively, flow piston 184 can be divided into an outer flow piston, which is sized and dimensioned to push fluid into the outer membrane, and a lumen flow piston, which is sized and dimensioned to push fluid into the lumen membrane.

Figure 18A:
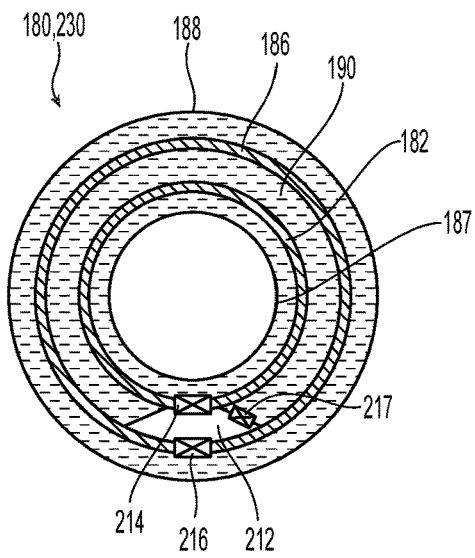
FIG. 18A is another cross-sectional view of an exemplary fluid reservoir of the cannula of FIGS. 17A-C showing a drainage channel and FIG. 18B is a partial cross-sectional view of an exemplary activator that opens the pressurized membranes.
Figure 18B:
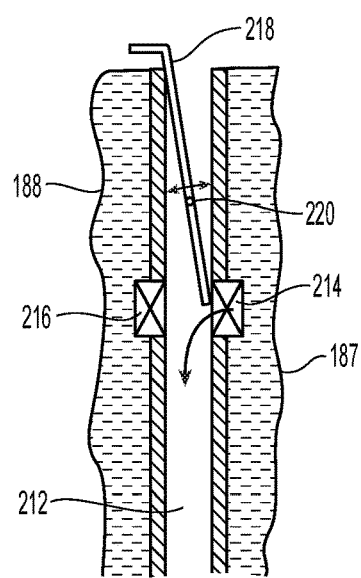

To remove/insert medical instruments into cannula 180 or to remove cannula 180 after the procedure, the fluid in the membranes can exit to reduce the pressure to allow extraction. Referring to FIG. 18A, vertical drainage channel 212 is provided preferably along the longitudinal axis of cannula 180. This drainage channel is fluidly connected to lumen membrane 187 via one-way valve 214 and to outer anchor membrane 188 via one-way valve 216. Preferably, valves 214 and 216 are flapper valve 200, where flapper 206 opens into or toward the membranes. An activator 218 can selectively open either valve 214 or 216. As shown in FIG. 18B, activator 218 is a pivoted latch or a rocker that pivots about axis 220. Rocker 218 may open one-way valve 214 to allow fluid in the lumen membrane to drain, and rocker 218 can be pivoted in the other direction to open one-way valve 216 to drain the outer anchor membrane 188. A third one-way valve 217 preferably located below the distal end of either lumen membrane 187 or outer anchor membrane 188 within drainage channel 212 that can be opened by activator 218 to release fluid from fluid chamber 190, so that the piston 184 can be depressed to provide better access to the lumen.

One-way valve 214 and 216, as well as activator 218, can be replaced by normally closed valve 169, shown in FIGS. 13C-D, with heads (d) extended externally. The lumen membrane and the outer anchor membrane can be individually drained by the surgeons by activating valve 169, by pushing on head (d) associated with each valve (169).

Figure 18C:
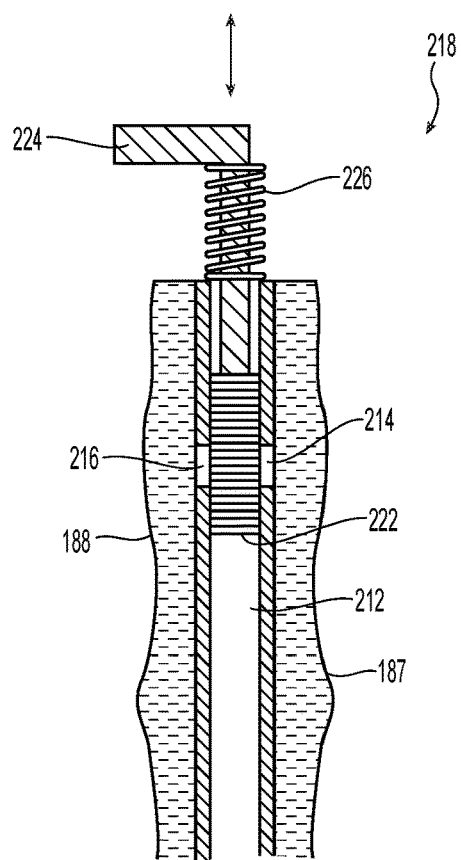
FIG. 18C is another cross-sectional view of another exemplary activator.

Another embodiment of activator 218 is illustrated in FIG. 18C. As shown, activator 218 comprises a sealing member 222 disposed in drainage channel 212 and attached to a piston 224. Valve 214 and 216 are simple openings that are sealed by sealing member 222, as shown. To drain membranes 187 and 188, piston 224 and sealing member 222 are pulled upward to expose openings 214 and 216 and fluid/liquid within the membranes would drain downward preferably into the body cavity. As illustrated, openings 214 and 216 are located at the same level to drain both membranes at the same time. Alternatively, one opening can be positioned lower to drain the membrane associated with the lower opening. Another substantially similar spring-biased activator 218 within the same drainage channel 212 is provided to open and close one-way valve or opening 217, which is preferably located at a lower elevation, to drain fluid chamber 190.

Alternatively, there can be two pistons/sealing member 222, 224, one for each membrane, to allow for selective decompression of the membranes. For instance, one can decompress the inner membrane, allowing for the egress/ingress of instruments while keeping the outer membrane inflated, so as not to disturb the position of the cannula and to keep it sealed to the body. The other can allow repositioning of the cannula without breaking the seal of the inner membrane so as to prevent leaking through the cannula. Alternatively, a compression spring 226 is place below the top of piston 224, such that spring 226 is compressed before either valve 214 or 216 is opened.

Advantageously, if flow piston 184 protrudes too far above outer casing 186/lumen wall 182 and obstructs the ingress or egress of medical instruments through the cannula's lumen, activator 218 can open either valve/opening 214 or 216 or both to drain fluid so that flow piston can be further depressed in direction 210. Alternatively, activator 218 can open valve 217 to drain fluid from fluid chamber 190 to lower flow piston 184, as discussed above.

Figure 20A:
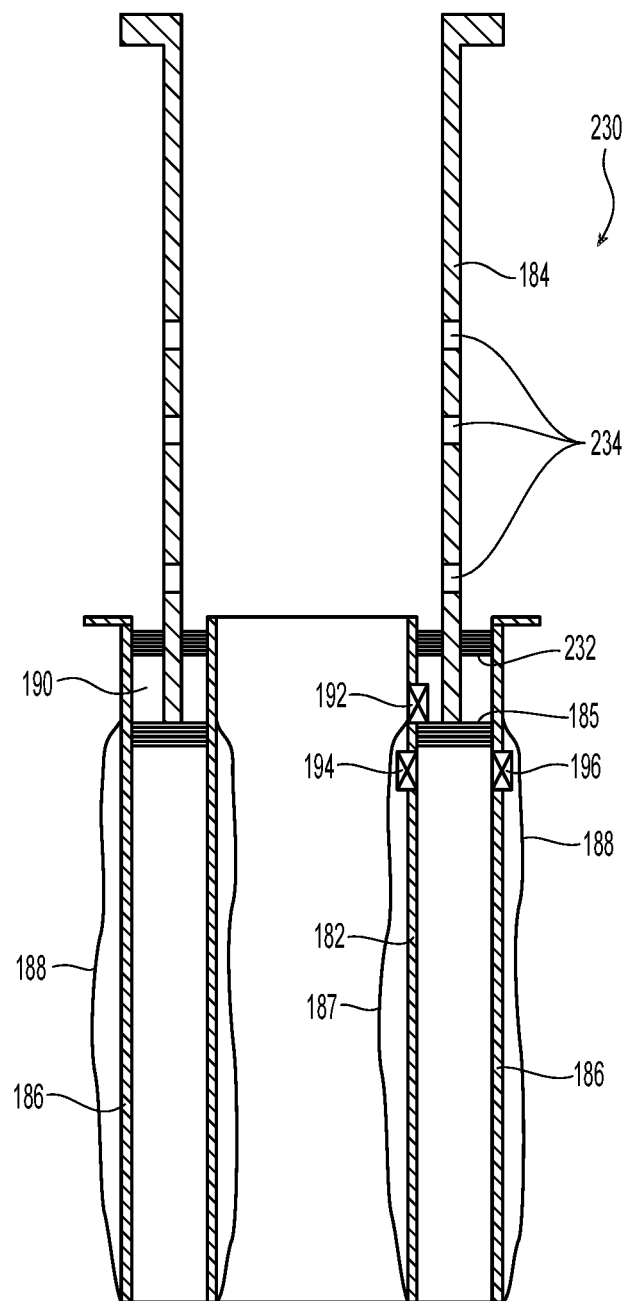
FIGS. 20A-C are cross-sectional views of another version of the embodiment shown in FIGS. 17A-C.
Figure 20C:
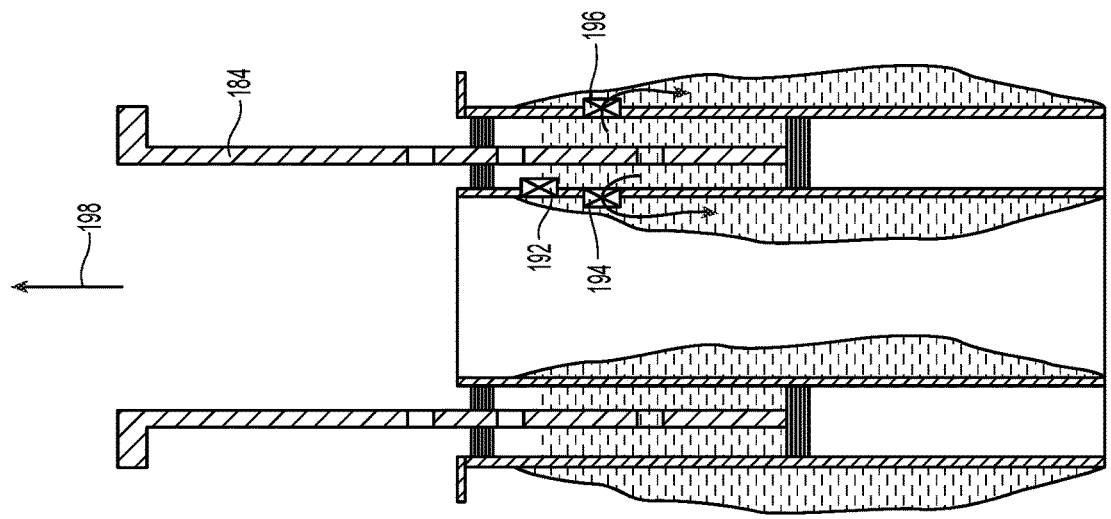
Figure 20B:
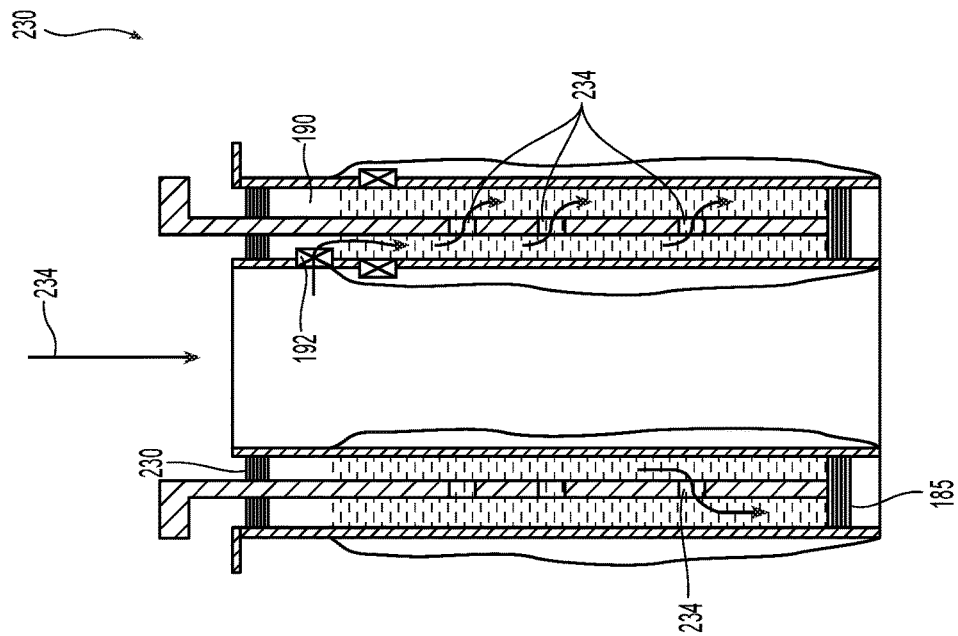

Another version of cannula 180 is shown in FIGS. 20A-C. Cannula 230 also primes the syringe-type cannula on a first stroke to fill fluid chamber 190 and on a second stroke pushes the fluid in fluid chamber 190 out to either lumen membrane 187 or anchor membrane 188 or both. Both cannulas 180 and 230 can be pumped multiple times to get fluid into fluid chamber 190 and to get fluid from fluid chamber 190 out to the membranes. The differences are that the first stroke is a downward stroke and the second stroke is an upward stroke. For clarity, components that perform the same function or are the same or substantially the same are assigned the same reference numbers.

As shown in FIG. 20A, cannula 230 is in the initial configuration before any fluid is pumped into fluid chamber 190, which in this embodiment is located behind distal seal 185 and is closed off by proximal seal 232. Inlet or reservoir valve 192 is located proximally, between distal and proximal seals 185, 232. Optionally, a hollow tube is connected to reservoir valve 192 and extends into the body cavity to access insufflated fluid. As flow piston is pushed downward or distally in direction 210, it creates a vacuum that opens reservoir valve 192, which as discussed above is a one-way valve and opens in the direction of the flow shown in FIG. 20B. Preferably, piston 184 is discontinuous so that fluid can cross-flow or can move from the inside of flow piston 184 to the outside of flow piston 184. For example, the surface of piston 184 may comprise a number of spokes or a truss, such as bridge or roof supporting structures. Alternatively, flow piston 184 may have a continuous surface with at least one opening 234 to allow fluid to cross-flow so that fluid can move from the inside of flow piston 184 to the outside of flow piston 184. Filling fluid chamber 190 is the second configuration of cannula 230.

To push fluid into the membranes, piston 184 is pulled in direction 198 as shown in FIG. 20C. This motion pushes fluid out of lumen one-way valve 194 and casing one-way valve 196. It is noted that FIG. 20C only shows flow piston 184 only partially pulled up. This shows the filling configuration of cannula 230. Flow piston 184 can be moved multiple times in directions 198 and 210 to fully install cannula 230. Other components of cannula 180, including but not limited to, those shown in FIGS. 18A-C and 19 are preferably included with cannula 230. For example, drainage channel 212 with lumen/casing/fluid chamber drainage valve/opening 214, 216, 217, drainage activator 218, etc. can be used with cannula 230.

Figure 21C:
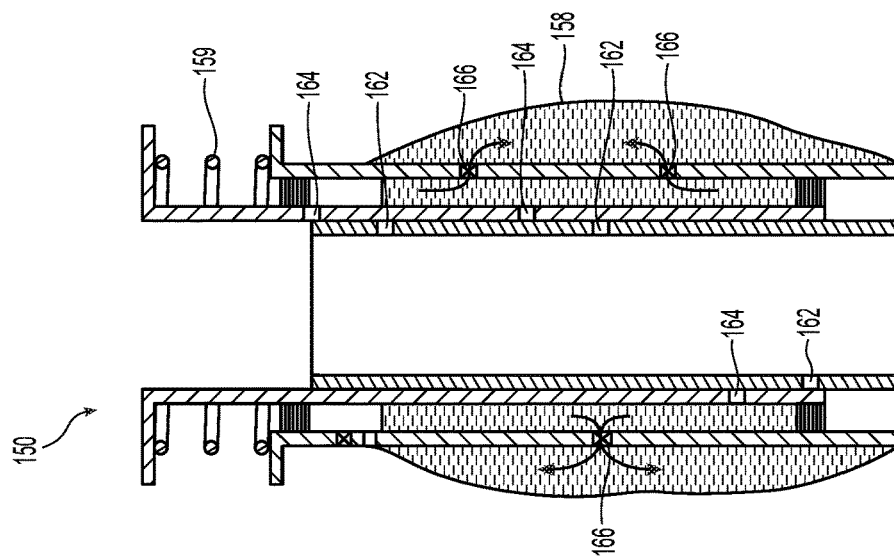
FIGS. 21A-C are cross-sectional views of another version of the embodiment shown in FIGS. 13 and 14 and their subparts.
Figure 21B:
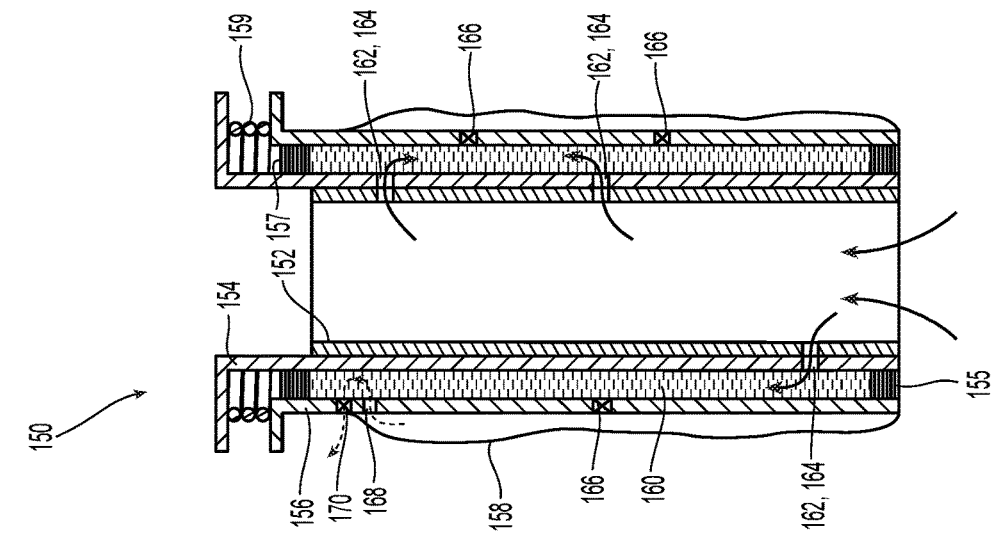
Figure 21A:
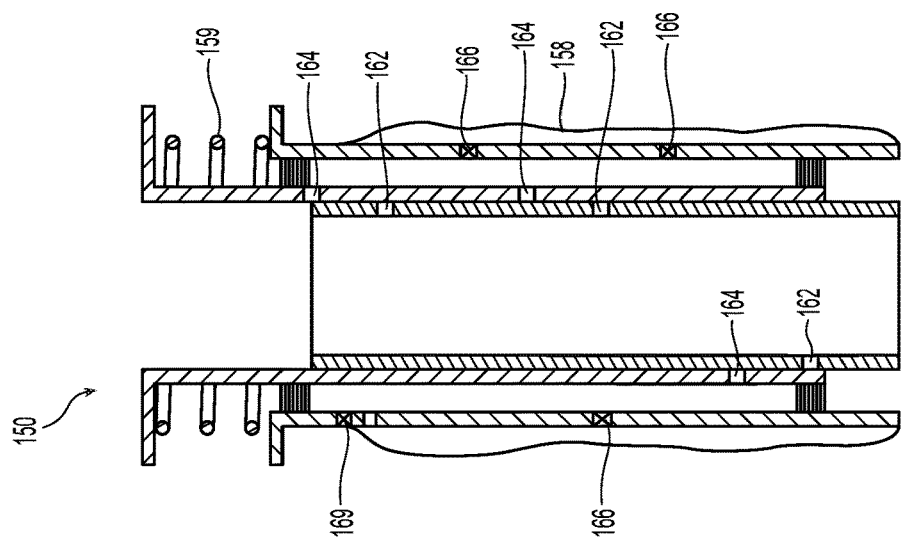
Figure 22A:
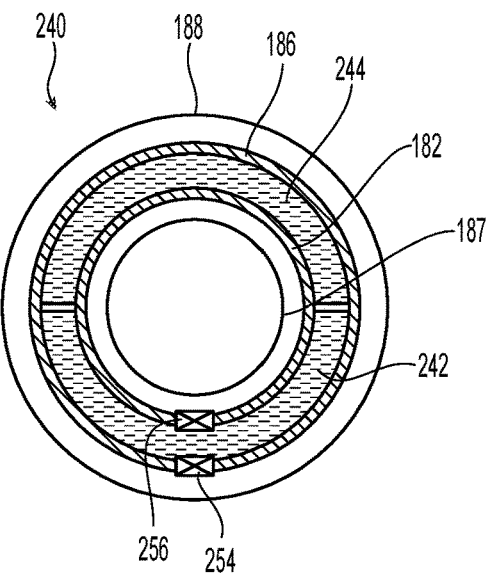
FIG. 22A is a cross-sectional view of a pre-filled cannula and FIG. 22B is a cross-sectional view of the piston for use with this pre-filled cannula.
Figure 22B:
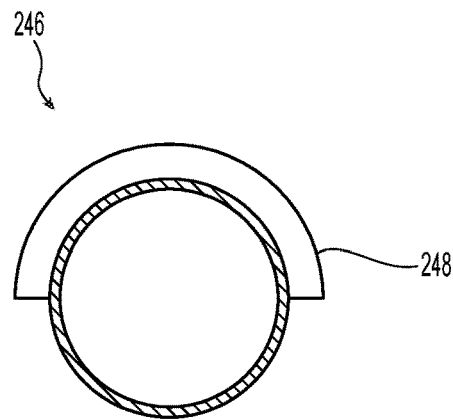

In yet another embodiment as shown in FIGS. 21A-C, cannula 150 is modified to be a hybrid version such that it pumps cavity fluid into fluid chamber. In this version, in the initial configuration with no fluid in the cannula shown in FIG. 21A, flow piston 154 is positioned relatively high, where lumen ports 162 and piston ports 164 are misaligned, as illustrated in FIG. 13B. A one-way valve such as flapper valve 200 is positioned in outer casing port 166, so that fluid can only flow from fluid chamber 160 to outer membrane 158. Sealing member 172 and counter-balance member 174 can be omitted. Normally closed valve 169 is positioned in vent 170, as illustrated in FIGS. 13C and D. As flow piston 154 is depressed or moved distally as shown in FIG. 21B, sealing member 155 is so moved and one-way valve in outer casing port 166 remains closed and a partial vacuum is created in flow chamber 160, until lumen ports 162 and piston ports 164 are aligned. When aligned, the partial vacuum pulls cavity fluid into fluid chamber 160 with a positive force (proportional to the negative pressure x the area of the ports 162, 164). Preferably after the pressure within flow chamber 160 equalizes with the cavity pressure (or prior to pressure equalization but after some fluid has flowed into flow chamber 160) flow piston 154 is moved upward or proximally, as shown in FIG. 21C. This proximal motion misaligns lumen port 162 and piston ports 164 to stop fluid from flowing into flow chamber 160. This proximal motion also moves fluid from flow chamber 160 into outer anchor membrane 158. The distal-proximal-distal motions can be repeated to pump cavity fluid into flow chamber 160 and from flow chamber 160 to outer anchor membrane 158, respectively, until the cannula is properly seated in the incision site.

In this version, the first several pump strokes may prime flow chamber 160 until sufficient air is vented and cavity fluid can flow into flow chamber 160 and outer anchor casing 158. Normally closed valve 169 can be depressed to vent as necessary. An optional return spring 159 can be positioned between the horizontal finger support portions of flow piston 154 and outer casing 156. As flow piston 154 is depressed or moved distally, spring 159 is compressed and thereby stores energy. The compressed spring when flow piston is released moves flow piston 154 proximally or upward. The user only has to depress flow piston 154 manually.

The spring tension of return spring 159 preferably determines the pressure in outer membrane 158. When flow piston 154 doesn't return all the way to its original position between strokes, outer membrane 158 has reached the designed allowed pressure as determined by the spring tension. Releasing normally closed valve 169 in vent 170 can drain outer membrane 158 for removal or repositioning. This embodiment solves a potential issue of long cannula length when flow piston 154 is moved proximally and may remove the need for locking mechanisms shown in FIGS. 15 and 16. Return spring 159 will keep flow piston 154 up and the one-way valve at outer membrane port 166 would maintain the pressure in outer anchor membrane 158 until this pressure is released by valve 169 in vent 170.

This embodiment is simpler than the embodiment shown in FIGS. 13 and 14 in that sealing members 172 is omitted and no rotational movement of any part of the cannula is required. Furthermore, this cannula shown in FIGS. 21A-C is a pump type cannula, which differs from the cannula of FIGS. 13-14, which is a vent-free flow filled type cannula. Lumen ports 162 and piston ports 164 act like a valve with the alignment of the ports represents opening of the valve and misalignment of the ports represents a closing of the valve.

Figure 17C:
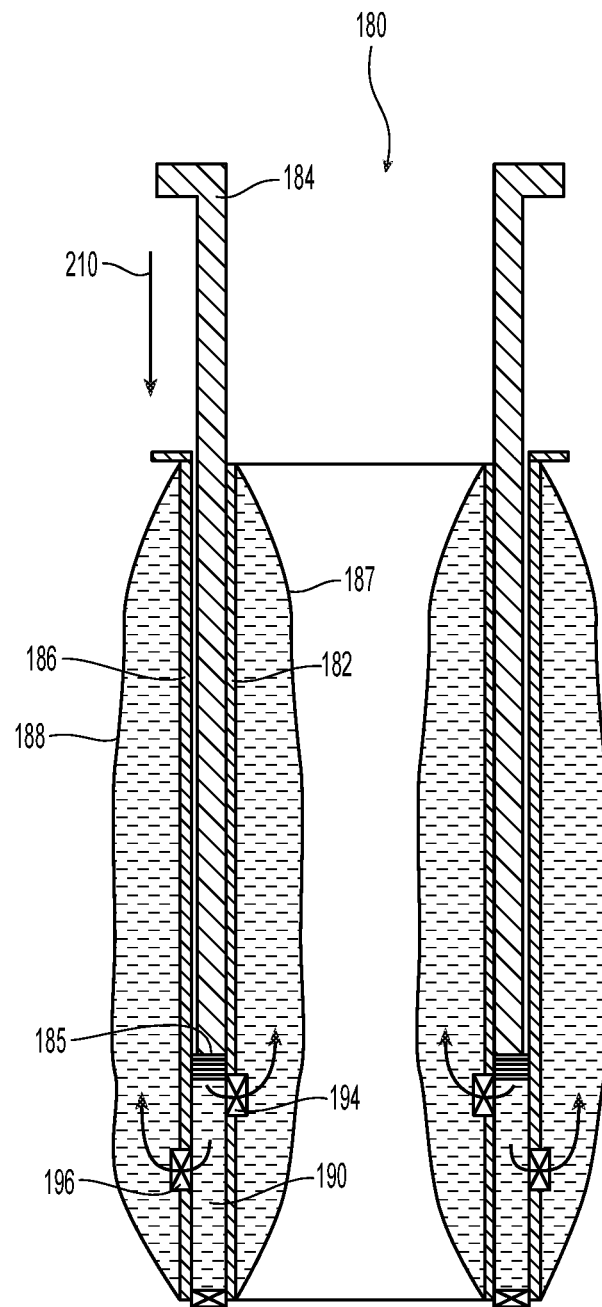

In another embodiment, fluid chamber 190 of cannulas 180 and 230, shown in FIGS. 17A-C and 20A-C, and in FIGS. 18A-C and 19, may be pre-filled with a fluid, such as surgical grade saline solution. Piston 184 may be moved in direction 210 in the case of cannula 180, as shown in FIG. 17C, or in direction 198 in the case of cannula 230, as shown in FIG. 20C, to fill and pressurize outer anchor membrane 188 and/or lumen membrane 187, without having to prime or fill fluid chamber 190. If necessary, a syringe can re-fill fluid chamber 190 to provide more fluid to inflate and pressurize the membranes. A valve such as those described herein can be provided to release fluid from one or more membranes to allow the withdrawal of the cannula or medical instruments.

One exemplary pre-filled cannula 240 is illustrated in FIG. 22 and its subparts. As shown in FIG. 22A, cannula 240 comprises a first flow chamber 242 and second flow chamber 244. While these two flow chambers are shown as having substantially equal volume, first flow chamber 242 may be larger than second flow chamber 244, or vice versa. First flow chamber 242 is sized and dimensioned to fill at least outer anchor membrane 188 fully, and optionally to fill lumen membrane 187 fully. Second flow chamber 244 is designed to top-off or to further pressurize outer anchor membrane 188 and optionally lumen membrane 187, if/when necessary. In this embodiment, sealing member 250 of first flow chamber 242 is located at the top, and sealing member 252 of second flow chamber 244 is located at the bottom, as shown in FIG. 22C. Preferably, piston 246 has rotatable pusher 248, as shown in FIG. 22B, positioned on top of sealing member 250 of the first flow chamber 242 on the downward stroke, as shown in FIG. 22C, to inflate/pressurize outer membrane 188 through valve 254 and optionally lumen membrane through valve 256. The downward stroke of piston 246 preferably does not move fluid out of second flow chamber 244, since sealing member 252 is located at the bottom of second flow chamber 244, as shown in FIG. 22D.

Figure 22C:
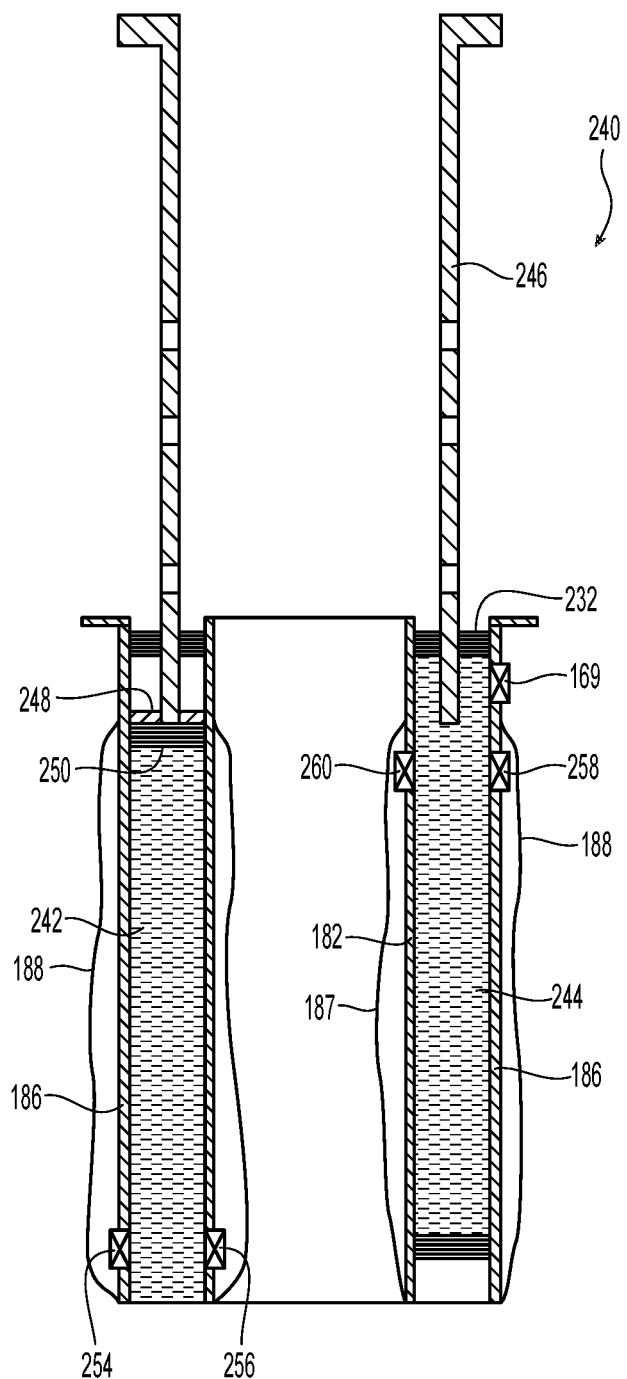
FIGS. 22C-F are lengthwise cross-sectional views of a sequence of operation of this pre-filled cannula.
Figure 22F:
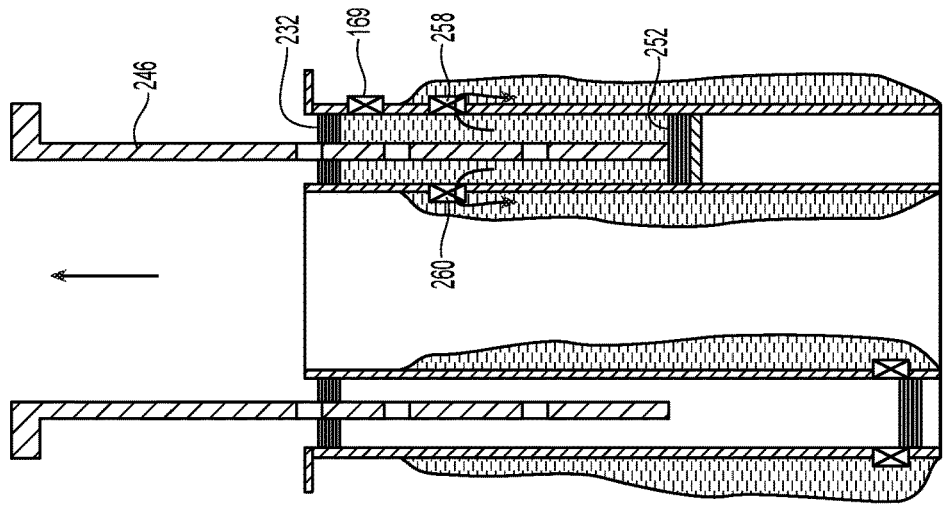
Figure 22E:
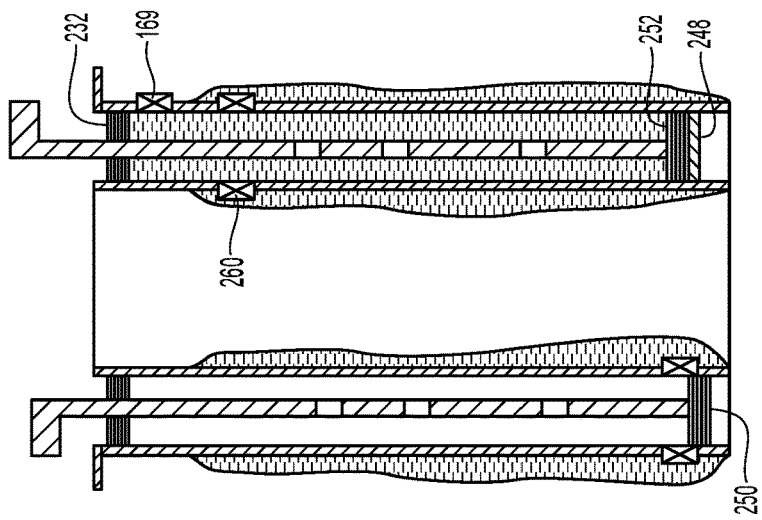
Figure 22D:
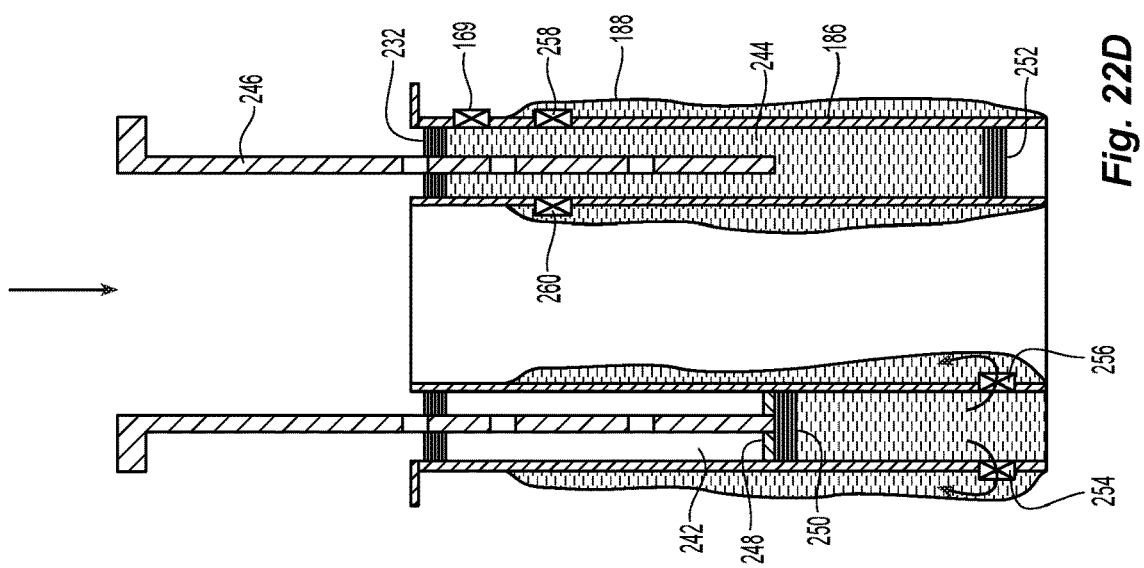

At the end of the downward stroke, preferably the outer anchor membrane and optionally the lumen membrane is fully inflated and pressurized. If not or if the cannula becomes loose during use, cannula 240 may use the fluid in second flow chamber 244 to re-inflate or top-off outer membrane 188. In this configuration, piston 246 is rotated so that pusher 248 is positioned below seal 252 of second flow chamber 244, as shown in FIG. 22E. In FIG. 22F, piston 246 is pulled upward and pusher 248 pulls sealing member 252 of second chamber 244 to push fluid through valve 258 to outer membrane 188 and optionally through valve 260 to lumen membrane 187, as shown in FIG. 22F.

Preferably, second flow chamber 244 has a normally closed valve, such as valve 169 discussed above, located at the top end. The surgeon can press on head "d" to open valve 169 to vent second flow chamber 244, so that piston 246 can be pushed downward to be substantially flushed with a top surface of cannula 240 and would not obstruct the lumen. Piston 246 can be pulled up repeatedly to re-inflate outer membrane 188 and be pushed back down by activating valve 169. It is noted that air or another gas may be pushed into outer membrane 188 and optionally lumen membrane 187; however, although air is more compressible than a liquid air is sufficiently incompressible to inflate the outer membrane 188 and lumen membrane 187.

Figure 23A:
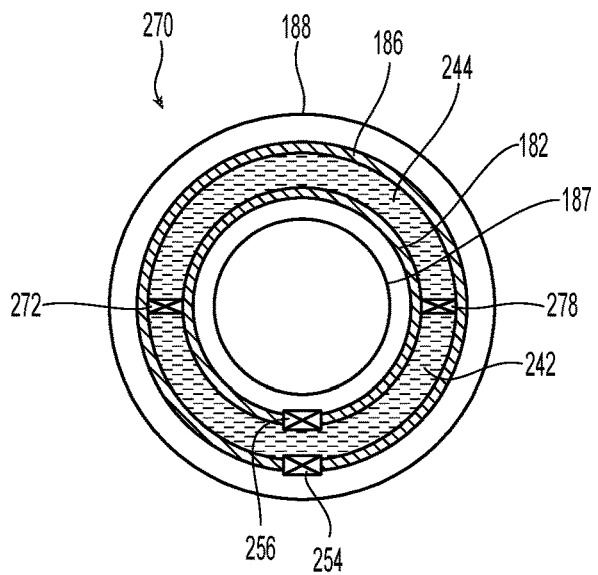
FIG. 23A is a cross-sectional view of a hybrid pre-filled cannula that pumps external fluid.
Figure 23B:
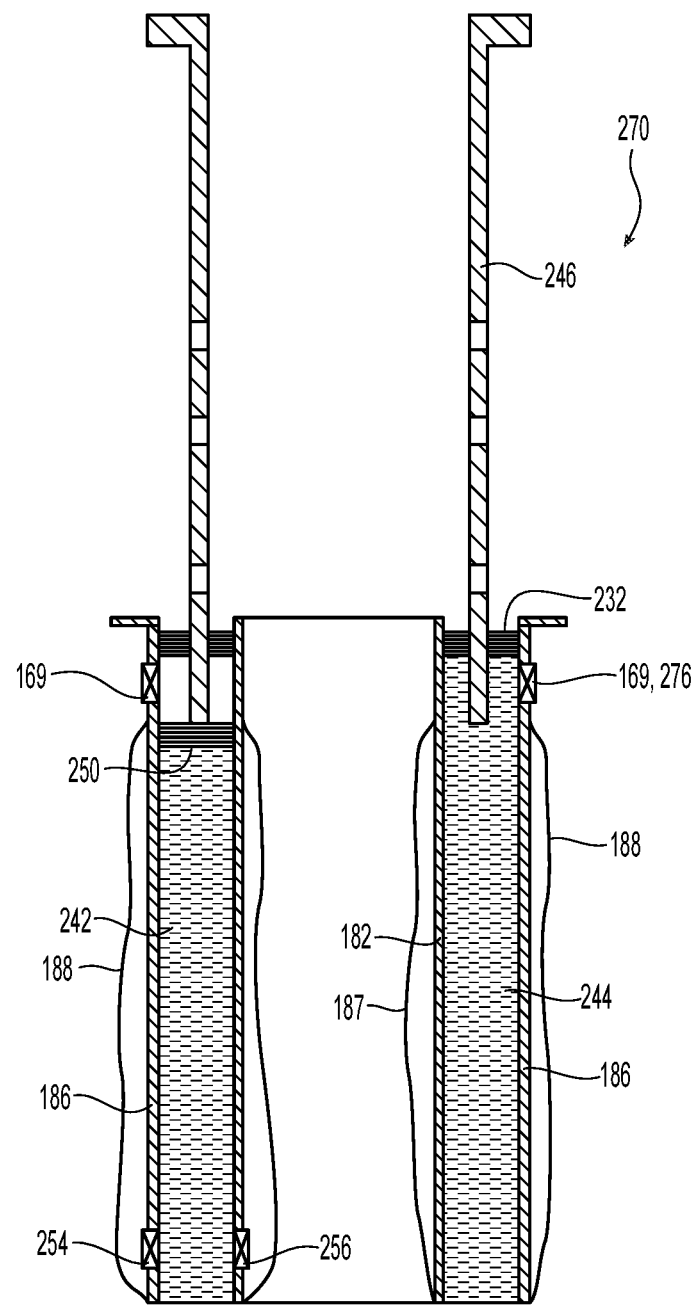

Another pre-filled cannula 270 is illustrated in FIG. 23 and its subparts. Cannula 270 is a hybrid cannula that can pump external fluid into the outer and lumen membranes. This cannula also has a first flow chamber 242 and second flow chamber 244, which are optionally prefilled, as shown in FIGS. 23A-B. First flow chamber 242 is connected to outer membrane 188 by one-way valve 254 and optionally to lumen membrane 187 by one-way valve 256. In this embodiment, the first and second flow chambers are connected together at least by one-way valve 272 to allow fluid from second flow chamber 244 to refill first flow chamber 242. Furthermore, pusher 248 of piston 246 is fixedly attached to sealing member 250 of first flow chamber 242, such that sealing member 250 moves up and down with piston 246. Piston 246 in this embodiment of cannula 270 does not displace fluid in second flow chamber 244.

Similar to cannula 240, when piston 246 of cannula 270 is pushed downward the fluid contained therein flows from first flow chamber 242 through valve 254 into outer membrane 188 and optionally through valve 256 into lumen membrane 187, as shown in FIG. 23C. Piston 246 is then pulled upward which creates a partial vacuum in first flow chamber 242, as illustrated in FIGS. 23D-E. This partial vacuum pulls fluid from second flow chamber 244 through one-way valve 272, as shown in FIG. 23A, to refill first flow chamber 242. These strokes can be repeated until outer membrane 188 and optionally lumen membrane 187 are full. If additional fluid is needed, a supply valve 272 located on top of second flow chamber 244 is provided for additional fluid to resupply the second flow chamber. Alternatively, supply valve 272 may be an opening allowing a tube to extend into second flow chamber 244. Second flow chamber 244 can be resupplied by any conventional means, such as a syringe, or micro pump.

When outer membrane 188 is properly filled and pressurized and if the elevation of piston 246 is high, then piston 246 can be pressed downward to be substantially flushed with the top of cannula 270 by releasing a small amount of fluid from outer membrane 188 via a valve similar to valve 169 to the outside described above, so that piston 246 can be pushed down and any displaced fluid can go into outer membrane 188 to take the place of the just released fluid. Alternatively, another one-way valve 278 connecting first flow chamber 242 to second flow chamber 244 is provided to allow fluid to flow from first flow chamber 242 to second flow chamber 244. Valve 278 should have an opening pressure that is higher than the pressure in outer anchor membrane 188 when it is properly filled and pressurized, so that valve 278 only opens when outer anchor membrane 188 is properly filled and pressurized and remains closed when outer anchor membrane 188 is being filled.

Normally closed valve 169 including vents 168 and 169 and preferably with membrane (h), as illustrated in FIGS. 13C-D can be included near the top of any of the cannulas illustrated herein to vent gas or liquid from the outer membrane in these inventive cannulas.

Return spring 159, discussed above, can be used with any cannula that requires the up and down movements of the piston or flow piston, including but not limited to, any All flow channels described herein can be channels that are etched or formed in or on the body of the lumen wall or external casing, for example by 3-D printing. However, these flow channels can also be hollow tubes formed separately and attached, for example by adhesive or otherwise attached, to the cannula.

Additionally, the casing anchor membrane and the optional lumen membrane discussed herein can be made from flexible material, such as a polymeric material. The casing anchor membrane and the optional lumen membrane discussed herein may also be made from an elastic material, i.e., a material that substantially returns to its original shape and/or dimensions when an applied force or an applied pressure is removed.

Lumen membranes, such as membrane 36, 104 and 187, can be replaced by a lumen diaphragm with slits cut thereon to allow medical instruments to pass through and are sufficiently resilient to seal around the medical instruments. Hence, lumen membrane 36, 104 and 187 are optional and can be omitted. Alternatively, cannula 10, 100, 150, 180, 230, 240, 270 may only have lumen membrane 36, 104, 187 and anchor or outer channel/membrane 16, 106, 158, 188 is omitted.

For the embodiments discussed herein, preferably the pressure in the anchor channel or membrane 16, 106, 158, 188 is pressurized when medical instruments are withdrawn from or inserted through the cannula 100, 10 to ensure that the cannula remains in position. While preferably the pressure in the lumen membrane 36, 104, 187 may optionally remain at substantially the same pressure as the cavity pressure or insufflated pressure.

It is noted that air or another gas may be used to inflate and pressurize the outer membrane(s) and the lumen membrane of all the embodiments described herein. Although air is more compressible than a liquid, air is sufficiently incompressible to inflate the outer membranes and lumen membranes.

Various components of one embodiment of the inventive cannula can be used with the other embodiment(s) of the inventive cannula. For example, members 12, 14, 16 of the casing in the embodiment shown in FIGS. 1-4 can be used as the casing for the embodiments shown in FIGS. 7-11. In another example, the cap 110, bellows 114 and manifold 108 of the embodiments in FIGS. 7-11 can be used with members 12, 14, 16 of the casing of the embodiment shown in FIGS. 1-4. Other combinations or sub-combinations can also be utilized.

Another summary of some of the cannulas is presented in claim format, as follows:

1. A cannula comprising:
a casing defining a lumen sized and dimensioned to receive one or more medical instruments,
an inflatable outer membrane attached to an outer surface of the casing,
a plurality of flow channels formed on or within the casing, wherein at least one flow channel is fluidly connected to the outer membrane to inflate the outer membrane and at least one flow channel is fluidly connected to the outer membrane to pressurize and/or to vent the outer membrane,
a flow selector to select one or more flow channels, and
a pressure source selectively connected to the outer membrane to pressurize the outer membrane,
wherein the outer membrane is filled with a fluid after the cannula is inserted into an incision site, and the pressure source pressurizes the outer membrane above a pressure of an insufflated fluid to maintain the cannula within the incision site.

2. The cannula of claim 1, wherein the casing comprises at least two layers, a first casing and a second casing layer, and the at least one flow channel is etched into the first casing layer and is covered by the second casing layer.

3. The cannula of claim 2, wherein the first casing layer is rotatable relative to the second casing layer so selectively open or close the plurality of flow channels.

4. The cannula of claim 3, wherein the flow selector comprises a first control dial and a second control dial and wherein the first casing layer and the second casing layer are connected to the first control dial and the second control dial, respectively.

5. The cannula of claim 4, wherein a port allowing the insufflated fluid to enter the outer membrane is located at a distal end of the casing.

6. The cannula of claim 1, wherein the pressure source comprises a rigid sleeve displacing the insufflated fluid in the outer membrane.

A summary of a method for operating the cannulas is presented in claim format, as follows:

7. A method for operating a cannula comprising the steps of
 a. inserting the cannula into an incision site,
 b. filling an outer membrane of the cannula with a fluid,
 c. sealing said outer membrane, and
 d. increasing a pressure inside the outer membrane above a pressure of an insufflated fluid.

8. The method of claim 7, wherein step (d) comprises a step of pumping another amount of fluid into the outer membrane.

9. The method of claim 8, wherein the step of pumping comprising a step of activating a bellows filled at least with the another amount of fluid into the outer membrane.

10. The method of claim 9, wherein a rotating mechanism compresses the bellows.

11. The method of claim 7 further comprising a step (e) of rotating a rotatable layer to select between step (b), (c) or (d).

While it is apparent that the illustrative embodiments of the invention disclosed herein fulfill the objectives stated above, it is appreciated that numerous modifications and other embodiments may be devised by those skilled in the art. One such modification is that instead of three tabs on the second embodiment, one tab can be used with different positions to open inner, outer, both, or none. Also, the inventive cannula may only have the inner membrane or may only have the outer membrane, or have an inner diaphragm instead of the inner membrane. Therefore, it will be understood that the appended claims are intended to cover all such modifications and embodiments, which would come within the spirit and scope of the present invention.

What is claimed is:

1. A cannula adapted to be inserted into a body cavity comprising
 a lumen wall and an outer casing positioned spaced apart from each other defining a fluid chamber therebetween;
 a flow piston connected to a sealing member which is positioned inside the fluid chamber, and
 an outer membrane connected to the outer casing,
 wherein the fluid chamber is fluidly connected to the outer membrane through an outer casing one-way valve,
 wherein in a priming configuration the fluid chamber is filled with a fluid, and
 wherein in a pressurizing configuration the flow piston is moved in a second direction to push the fluid from the fluid chamber into the outer membrane through the casing one-way valve.

2. The cannula of claim 1, wherein the fluid chamber is fluidly connected to the body cavity by a reservoir one-way valve, and wherein in the priming configuration the flow piston is moved in a first direction to move the fluid into the fluid chamber through the reservoir one-way valve.

3. The cannula of claim 2, wherein the first direction is a distal direction and the second direction is a proximal direction.

4. The cannula of claim 2, wherein the first direction is a proximal direction and the second direction is a distal direction.

5. The cannula of claim 2, wherein at least one of the casing one-way valve and the reservoir one-way valve comprises a flapper valve.

6. The cannula of claim 2, wherein the reservoir one-way valve is located proximate a distal end of the cannula.

7. The cannula of claim 2 further comprises a second sealing member to provide a seal for the fluid chamber and the reservoir one-way valve is located proximate a proximal end of the cannula.

8. The cannula of claim 1 further comprising a lumen membrane connected to the lumen wall and wherein the fluid chamber is fluidly connected to the lumen membrane through a lumen valve, and in the pressurizing configuration the fluid is pushed into the lumen membrane through the lumen valve.

9. The cannula of claim 8, wherein the lumen valve comprises a one-way valve.

10. The cannula of claim 1, wherein the flow piston is located adjacent to the lumen wall and the flow piston comprises at least one piston port and the lumen wall comprises at least one lumen port, and wherein in the priming configuration the at least one piston port and the at least one lumen port align with each other to form an open state of a lumen valve and wherein in the pressurizing configuration the at least one piston port and the at least one lumen port misalign with each other to form a closed state of the lumen valve.

11. The cannula of claim 1 further comprising a drainage channel, wherein the drainage channel is fluidly connected to the outer membrane by a valve and wherein said valve can be opened by an activator to drain the fluid from the outer membrane to the drainage channel.

12. The cannula of claim 1 further comprising a drainage channel, wherein the drainage channel is fluidly connected to the outer membrane by a drainage opening, wherein the opening is sealed by a drainage sealing member in the pressurizing configuration and in a drainage configuration the drainage sealing member is moved to expose the drainage opening.

13. The cannula of claim 1, wherein the outer membrane is made from an elastomeric material.

14. The cannula of claim 1 further comprising a vent valve positioned to vent the outer membrane.

15. The cannula of claim 14, wherein the vent valve further comprises a first vent in fluid communication with the outer membrane and a second vent in fluid communication with the first vent.

16. The cannula of claim 15, wherein a user-actuatable normally closed valve is positioned in the second vent.

17. The cannula of claim 1, wherein the priming configuration comprises a pre-filled configuration outside of the body cavity.

* * * * *